United States Patent [19]
Birkenbach et al.

[11] Patent Number: 5,744,301
[45] Date of Patent: Apr. 28, 1998

[54] METHODS OF DETECTION OF EPSTEIN BARR VIRUS INDUCED GENES EXPRESSED IN THE PLACENTA

[75] Inventors: Mark Birkenbach, Tinley Park, Ill.; Elliott Kieff, Brookline, Mass.

[73] Assignee: Brigham and Women's Hospital, Boston, Mass.

[21] Appl. No.: 383,750

[22] Filed: Feb. 2, 1995

Related U.S. Application Data

[63] Continuation-in-part of Ser. No. 352,678, Nov. 30, 1994, which is a continuation of Ser. No. 980,518, Nov. 25, 1992, abandoned.

[51] Int. Cl.$^6$ .................................................. C12Q 1/68
[52] U.S. Cl. ............................ 435/6; 514/44; 536/23.5; 435/5
[58] Field of Search .................. 514/44; 435/5, 435/6; 536/24.5, 23.5

[56] References Cited

FOREIGN PATENT DOCUMENTS

WO 94/12519  6/1994  WIPO .

OTHER PUBLICATIONS

Stein et al., Science, 261:1004–1012, Aug. 1993.
Brown, Washington Post, p. A1 and A22, "Gene Therapy Oversold by Researchers, Journalists", Dec. 1995.
Alfieri et al., "Early Events in Epstein–Barr Virus Infection of Human B Lymphocytes," *Virology* 181:595–608 (1991).
Bayliss et al., "An Immunoprecipitation Blocking Assay for the Analysis of EBV Induced Antigens," *J. Virol. Meth.* 7:229–239 (1983).
Bayliss et al., "The Regulated Expression of Epstein–Barr Virus. III. Proteins Specified by EBV During the Lytic Cycle," *J. gen. Virol.* 56:105–118 (1981).
Birkenbach et al., "Epstein–Barr Virus Latent Infection Membrane Protein Increases Vimentin Expression in Human B–Cell Lines," *J. Virol.* 63(9):4079–4084 (1989).
Calender et al., "Epstein–Barr Virus (EBV) Induces Expression of B–Cell Activation Markers on in Vitro Infection of EBV–Negative B–Lymphoma Cells," *PNAS USA* 84:8060–8064 (1987).
Ehlin-Hendriksson et al., "Expression of B–Cell–Specific Markers in Different Burkitt Lymphoma Subgroups," *Intl. J. Cancer* 39:211–218 (1987).
Favrot et al., "EBV–Negative and –Positive Burkitt Cell Lines Variably Express Receptors for B–Cell Activation and Differentiation," *Intl. J. Cancer* 38:901–906 (1986).
Gregory et al., "Different Epstein–Barr Virus–B Cell Interactions in Phenotypically Distinct Clones of a Burkitt's Lymphoma Cell Line," *J. gen. Virol.* 71:1481–1495 (1990).
Henderson et al., "Induction of bcl–2 Expression by Epstein– Barr Virus Latent Membrane Protein 1 Protects Infected B Cells from Programmed Cell Death," *Cell* 65:1107–1115 (1991).
Hummel, M. and Kieff, E., "Mapping of Polypeptides Encoded by the Epstein–Barr Virus Genome in Productive Infection," *PNAS USA* 79:5698–5702 (1982).
Knutson, J.C., "The Level of c–fgr RNA is Increased by EBNA–2, and Epstein–Barr Virus Gene Required for B–Cell," *J. Virol.* 64(6):2530–2536 (1990).

(List continued on next page.)

*Primary Examiner*—Scott W. Houtteman
*Attorney, Agent, or Firm*—Wolf, Greenfield and Sacks, P.C.

[57] ABSTRACT

The present invention relates, in general, to Epstein Barr virus induced (EBI) genes. In particular, the present invention relates to DNA segments coding for EBI 1, EBI 2, or EBI 3 polypeptides; EBI 1, EBI 2, or EBI 3 polypeptides; recombinant DNA molecules; cells containing the recombinant DNA molecules; antisense EBI 1, EBI 2, or EBI 3 constructs; antibodies having binding affinity to an EBI 1, EBI 2, or EBI 3 polypeptide; hybridomas containing the antibodies; nucleic acid probes for the detection of the presence of Epstein Barr Virus; a method of detecting Epstein Barr virus in a sample; and kits containing nucleic acid probes or antibodies.

3 Claims, 17 Drawing Sheets

EBI 3

OTHER PUBLICATIONS

Qualtiere, L.F. and Pearson, G.R., "Epstein–Barr Virus–Induced Membrane Antigens: Immunochemical Characterization of Triton X–100 Solubilized Viral Membrane Antigens from EBV–Superinfected Raji Cells," *Intl. J. Cancer* 23:808–817 (1979).

Rowe et al., "Differences in B Cell Growth Phenotype Reflect Novel Patterns of Epstein–Barr Virus Latent Gene Expression in Burkitt's Lymphoma Cells," *EMBO J.* 6(9):2743–2751 (1987).

Rowe et al., "Epstein–Barr Virus Status and Tumour Cell Phenotype in Sporadic Burkitt's Lymphoma," *Intl. J. Cancer* 37:367–373 (1986).

Spira et al., "Cell–Surface Immunoglobulin and Insulin Receptor Expression in an EBV–Negative Lymphoma Cell Line and Its EBV–Converted Sublines," *J. Immunol.* 126(1):122–126 (1981).

Stratagene Catalog, p. 39 (1988).

Thorley–Lawson et al., "Blast–2 [EBVCS], an Early Cell Surface Marker of Human B Cell Activation, is Superinduced by Epstein Barr Virus," *J. Immunol.* 134(5):3007–3012 (1985).

Wang et al., "Epstein–Barr Virus Latent Membrane Protein (LMP1) and Nuclear Proteins 2 and 3C are Effectors of Phenotypic Changes in B Lymphocytes: EBNA–2 and LMP1 Cooperatively Induce CD23," *J. Virol.* 64(5):2309–2318 (1990).

Wang et al., "Epstein–Barr Virus Nuclear Antigen 2 Specifically Induces Expression of the B–Cell Activation Antigen CD23," *PNAS USA* 84:3452–3456 (1987).

Wang et al., "Epstein–Barr Virus Nuclear Antigen 2 Transactivates Latent Membrane Protein LMP1," *J. Virol.* 64(7):3407–3416 (1990).

Watson et al., in: Molecular Biology of the Gene, 4th Edition, vol. I, Benjamin/Cummings, Publ., Menlo Park, CA, p. 276 (1987).

GGAATTCCGT AGTGCCGAGGC CGGGCACAGC CTTCCTGTGT GGTTTTACCG CCCAGAGAGC 60
• ••

| GTC ATG GAC CTG GGG AAA CCA ATG AAA AGC GTG CTG GTG GTG GCT CTC | 108 |
| Met Asp Leu Gly Lys Pro Met Lys Ser Val Leu Val Val Ala Leu | |
| 1     5          10            15 | |

| CTT GTC ATT TTC CAG GTA TGC CTG TGT CAA GAT GAG GTC ACG GAC GAT | 156 |
| Leu Val Ile Phe Gln Val Cys Leu Cys Gln Asp Glu Val Thr Asp Asp | |
|           20           25            30 | |

| TAC ATC GGA GAC AAC ACC ACA GTG GAC TAC ACT TTG TTC GAG TCT TTG | 204 |
| Tyr Ile Gly Asp Asn Thr Thr Val Asp Tyr Thr Leu Phe Glu Ser Leu | |
|     35 CHO ### ###    40            45 | |

| TGC TCC AAG AAG GAC GTG CGG AAC TTT AAA GCC TGG TTC CTC CCT ATC | 252 |
| Cys Ser Lys Lys Asp Val Arg Asn Phe Lys Ala Trp Phe Leu Pro Ile | |
|     50           55            60 | |

| ATG TAC TCC ATC ATT TGT TTC GTG GGC CTA CTG GGC AAT GGG CTG GTC | 300 |
| Met Tyr Ser Ile Ile Cys Phe Val Gly Leu Leu Gly Asn Gly Leu Val | |
|     65           70            75 | |

| GTG TTG ACC TAT ATC TAT TTC AAG AGG CTC AAG ACC ATG ACC GAT ACC | 348 |
| Val Leu Thr Tyr Ile Tyr Phe Lys Arg Leu Lys Thr Met Thr Asp Thr | |
|   80           85            90           95 | |

| TAC CTG CTC AAC CTG GCG GTG GCA GAC ATC CTC TTC CTC CTG ACC CTT | 396 |
| Tyr Leu Leu Asn Leu Ala Val Ala Asp Ile Leu Phe Leu Leu Thr Leu | |
|         100          105           110 | |

| CCC TTC TGG GCC TAC AGC GCG GCC AAG TCC TGG GTC TTC GGT GTC CAC | 444 |
| Pro Phe Trp Ala Tyr Ser Ala Ala Lys Ser Trp Val Phe Gly Val His | |
|         115          120           125 | |

| TTT TGC AAG CTC ATC TTT GCC ATC TAC AAG ATG AGC TTC TTC AGT GGC | 492 |
| Phe Cys Lys Leu Ile Phe Ala Ile Tyr Lys Met Ser Phe Phe Ser Gly | |
|         130          135           140 | |

| ATG CTC CTA CTT CTT TGC ATC AGC ATT GAC CGC TAC GTG GCC ATC GTC | 540 |
| Met Leu Leu Leu Leu Cys Ile Ser Ile Asp Arg Tyr Val Ala Ile Val | |
|         145          150           155 | |

FIG.1A-1

```
CAG GCT GTC TCA GCT CAC CGC CAC CGT GCC CGC GTC CTT CTC ATC AGC        588
Gln Ala Val Ser Ala His Arg His Arg Ala Arg Val Leu Leu Ile Ser
160             165             170             175

AAG CTG TCC TGT GTG GGC AGC GCC ATA CTA GCC ACA GTG CTC TCC ATC        636
Lys Leu Ser Cys Val Gly Ser Ala Ile Leu Ala Thr Val Leu Ser Ile
            180             185             190

CCA GAG CTC CTG TAC AGT GAC CTC CAG AGG AGC AGC AGT GAG CAA GCG        684
Pro Glu Leu Leu Tyr Ser Asp Leu Gln Arg Ser Ser Ser Glu Gln Ala
        195             200             205

ATG CGA TGC TCT CTC ATC ACA GAG CAT GTG GAG GCC TTT ATC ACC ATC        732
Met Arg Cys Ser Leu Ile Thr Glu His Val Glu Ala Phe Ile Thr Ile
        210             215             220

CAG GTG GCC CAG ATG GTG ATC GGC TTT CTG GTC CCC CTG CTG GCC ATG        780
Gln Val Ala Gln Met Val Ile Gly Phe Leu Val Pro Leu Leu Ala Met
    225             230             235

AGC TTC TGT TAC CTT GTC ATC ATC CGC ACC CTG CTC CAG GCA CGC AAC        828
Ser Phe Cys Tyr Leu Val Ile Ile Arg Thr Leu Leu Gln Ala Arg Asn
240             245             250             255

TTT GAG CGC AAC AAG GCC ATC AAG GTG ATC ATC GCT GTC GTC GTG GTC        876
Phe Glu Arg Asn Lys Ala Ile Lys Val Ile Ile Ala Val Val Val Val
            260             265             270

TTC ATA GTC TTC CAG CTG CCC TAC AAT GGG GTG GTC CTG GCC CAG ACG        924
Phe Ile Val Phe Gln Leu Pro Tyr Asn Gly Val Val Leu Ala Gln Thr
        275             280             285

GTG GCC AAC TTC AAC ATC ACC AGT AGC ACC TGT GAG CTC AGT AAG CAA        972
Val Ala Asn Phe Asn Ile Thr Ser Ser Thr Cys Glu Leu Ser Lys Gln
        290     CHO /// /// 295         300

CTC AAC ATC GCC TAC GAC GTC ACC TAC AGC CTG GCC TGC GTC CGC TGC       1020
Leu Asn Ile Ala Tyr Asp Val Thr Tyr Ser Leu Ala Cys Val Arg Cys
        305             310             315
```

FIG.1A-2

```
TGC GTC AAC CCT TTC TTG TAC GCC TTC ATC GGC GTC AAG TTC CGC AAC        1068
Cys Val Asn Pro Phe Leu Tyr Ala Phe Ile Gly Val Lys Phe Arg Asn
320             325             330             335

GAT ATC TTC AAG CTC TTC AAG GAC CTG GGC TGC CTC AGC CAG GAG CAG        1116
Asp Ile Phe Lys Leu Phe Lys Asp Leu Gly Cys Leu Ser Gln Glu Gln
        340             345             350

CTC CGG CAG TGG TCT TCC TGT CGG CAC ATC CGG CGC TCC TCC ATG AGT        1164
Leu Arg Gln Trp Ser Ser Cys Arg His Ile Arg Arg Ser Ser Met Ser
            355             360             365

GTG GAG GCC GAG ACC ACC ACC ACC TTC TCC CCA TAGGCGACTC TTCTGCCTGG      1217
Val Glu Ala Glu Thr Thr Thr Thr Phe Ser Pro ***
                370             375

ACTAGAGGGA CCTCTCCCAG GGTCCCTGGG GTGGGGATAG GGAGCAGATG CAATGACTCA      1277

GGACATCCCC CCGCCAAAAG CTGCTCAGGG GAAAAAGCAG CTCTCCCCTC AGAGTGCAAG      1337

CCCCTGCTCC AGAAGATAGC TTCACCCCAA TCCCAGCTAC CTCAACCAAT GCCAAAAAAA      1397

GACAGGGCTG ATAAGCTAAC ACCAGACAGA CAACACTGGG AAACAGAGGC TATTGTCCCC      1457

TAAACCAAAA ACTGAAAGTG AAAGTCCAGA AACTGTTCCC ACCTGCTGGA GTGAAGGGGC      1517

CAAGGAGGGT GAGTGCAAGG GGCGTGGGAG TGCCCTGAAG AGTCCTCTGA ATGAACCTTC      1577

TGGCCTCCCA CAGACTCAAA TGCTCAGACC AGCTCTTCCG AAAACCAGGC CTTATCTCCA      1637

AGACCAGAGA TAGTGGGGAG ACTTCTTGGC TTGGTGAGGA AAAGCGGACA TCAGCTGGTC      1697

AAACAAACTC TCTGAACCCC TCCCTCCATC GTTTTCTTCA CTGTCCTCCA AGCCAGCGGG      1757

AATGGCAGCT GCCACGCCGC CCTAAAAGCA CACTCATCCC CTCACTTGCC GCGTCGCCCT      1817

CCCAGGCTCT CAACAGGGGA GAGTGTGGTG TTTCCTGCAG GCCAGGCCAG CTGCCTCCGC      1877

GTGATCAAAG CCACACTCTG GGCTCCAGAG TGGGGATGAC ATGCACTCAG CTCTTGGCTC      1937
```

FIG.1A-3

```
CACTGGGATG GGAGGAGAGG ACAAGGGAAA TGTCAGGGGC GGGGAGGGTG ACAGTGGCCG    1997

CCCAAGGCCA CGAGCTTGTT CTTTGTTCTT TGTCACAGGG ACTGAAAACC TCTCCTCATG    2057

TTCTGCTTTC GATTCGTTAA GAGAGCAACA TTTTACCCAC ACACAGATAA AGTTTTCCCT    2117

TGAGGAAACA ACAGCTTTAA AAAAAAAAAA GGAATTC                             2154
```

FIG.1A-4

```
GGAATTCCCT GATATACACC TGGACCACCA CCA ATG GAT ATA CAA ATG GCA AAC  54
           * **                    Met Asp Ile Gln Met Ala Asn
                                    1               5
```

```
AAT TTT ACT CCG CCC TCT GCA ACT CCT CAG GGA AAT GAC TGT GAC CTC  102

Asn Phe Thr Pro Pro Ser Ala Thr Pro Gln Gly Asn Asp Cys Asp Leu
CHO ### ###
        10              15                  20
```

```
TAT GCA CAT CAC AGC ACG GCC AGG ATA GTA ATG CCT CTG CAT TAC AGC  150

Tyr Ala His His Ser Thr Ala Arg Ile Val Met Pro Leu His Tyr Ser
        25              30              35
```

```
CTC GTC TTC ATC ATT GGG CTC GTG GGA AAC TTA CTA GCC TTG GTC GTC  198

Leu Val Phe Ile Ile Gly Leu Val Gly Asn Leu Leu Ala Leu Val Val
        40              45              50              55
```

```
ATT GTT CAA AAC AGG AAA AAA ATC AAC TCT ACC ACC CTC TAT TCA ACA  246

Ile Val Gln Asn Arg Lys Lys Ile Asn Ser Thr Thr Leu Tyr Ser Thr
              60              65              70
```

```
AAT TTG GTG ATT TCT GAT ATA CTT TTT ACC ACG GCT TTG CCT ACA CGA  294

Asn Leu Val Ile Ser Asp Ile Leu Phe Thr Thr Ala Leu Pro Thr Arg
        75              80              85
```

```
ATA GCC TAC TAT GCA ATG GGC TTT GAC TGG AGA ATC GGA GAT GCC TTG  342

Ile Ala Tyr Tyr Ala Met Gly Phe Asp Trp Arg Ile Gly Asp Ala Leu
        90              95              100
```

```
TGT AGG ATA ACT GCG CTA GTG TTT TAC ATC AAC ACA TAT GCA GGT GTG  390

Cys Arg Ile Thr Ala Leu Val Phe Tyr Ile Asn Thr Tyr Ala Gly Val
        105             110             115
```

FIG.1B-1

```
AAC TTT ATG ACC TGC CTG AGT ATT GAC CGC TTC ATT GCT GTG GTG CAC 438

Asn Phe Met Thr Cys Leu Ser Ile Asp Arg Phe Ile Ala Val Val His
120             125             130             135

CCT CTA CGC TAC AAC AAG ATA AAA AGG ATT GAA CAT GCA AAA GGC GTG 486

Pro Leu Arg Tyr Asn Lys Ile Lys Arg Ile Glu His Ala Lys Gly Val
                140             145             150

TGC ATA TTT GTC TGG ATT CTA GTA TTT GCT CAG ACA CTC CCA CTC CTC 534

Cys Ile Phe Val Trp Ile Leu Val Phe Ala Gln Thr Leu Pro Leu Leu
        155             160             165

ATC AAC CCT ATG TCA AAG CAG GAG GCT GAA AGG ATT ACA TGC ATG GAG 582

Ile Asn Pro Met Ser Lys Gln Glu Ala Glu Arg Ile Thr Cys Met Glu
        170             175             180

TAT CCA AAC TTT GAA GAA ACT AAA TCT CTT CCC TGG ATT CTG CTT GGG 630

Tyr Pro Asn Phe Glu Glu Thr Lys Ser Leu Pro Trp Ile Leu Leu Gly
        185             190             195

GCA TGT TTC ATA GGA TAT GTA CTT CCA CTT ATA ATC ATT CTC ATC TGC 678

Ala Cys Phe Ile Gly Tyr Val Leu Pro Leu Ile Ile Ile Leu Ile Cys
200             205             210             215

TAT TCT CAG ATC TGC TGC AAA CTC TTC AGA ACT GCC AAA CAA AAC CCA 726

Tyr Ser Gln Ile Cys Cys Lys Leu Phe Arg Thr Ala Lys Gln Asn Pro
                220             225             230

CTC ACT GAG AAA TCT GGT GTA AAC AAA AAG GCT CTC AAC ACA ATT ATT 774

Leu Thr Glu Lys Ser Gly Val Asn Lys Lys Ala Leu Asn Thr Ile Ile
        235             240             245

CTT ATT ATT GTT GTG TTT GTT CTC TGT TTC ACA CCT TAC CAT GTT GCA 822

Leu Ile Ile Val Val Phe Val Leu Cys Phe Thr Pro Tyr His Val Ala
        250             255             260
```

FIG.1B-2

```
ATT ATT CAA CAT ATG ATT AAG AAG CTT CGT TTC TCT AAT TTC CTG GAA    870

Ile Ile Gln His Met Ile Lys Lys Leu Arg Phe Ser Asn Phe Leu Glu
    265             270             275

TGT AGC CAA AGA CAT TCG TTC CAG ATT TCT CTG CAC TTT ACA GTA TGC    918

Cys Ser Gln Arg His Ser Phe Gln Ile Ser Leu His Phe Thr Val Cys
280             285             290             295

CTG ATG AAC TTC AAT TGC TGC ATG GAC CCT TTT ATC TAC TTC TTT GCA    966

Leu Met Asn Phe Asn Cys Cys Met Asp Pro Phe Ile Tyr Phe Phe Ala
         300             305             310

TGT AAA GGG TAT AAG AGA AAG GTT ATG AGG ATG CTG AAA CGG CAA GTC    1014

Cys Lys Gly Tyr Lys Arg Lys Val Met Arg Met Leu Lys Arg Gln Val
         315             320             325

AGT GTA TCG ATT TCT AGT GCT GTG AAG TCA GCC CCT GAA GAA AAT TCA    1062

Ser Val Ser Ile Ser Ser Ala Val Lys Ser Ala Pro Glu Glu Asn Ser
         330             335             340

CGT GAA ATG ACA GAA ACG CAG ATG ATG ATA CAT TCC AAG TCT TCA AAT    1110

Arg Glu Met Thr Glu Thr Gln Met Met Ile His Ser Lys Ser Ser Asn
         345             350             355

GGA AAG TGAAATGGAT TGTATTTTGG TTTATAGTGA CGTAAACTGT ATGACAAACT     1166

Gly Lys •••
360

TTGCAGGACT TCCCTTATAA AGCAAAATAA TTGTTCAGCT TCCAATTAGT ATTCTTTTAT 1226

ATTTCTTTCA TTGGGCGCTT TCCCATCTCC AACTCGGAAG TAAGCCCAAG AGAACAACAT 1286

AAAGCAAACA ACATAAAGCA CAATAAAAAT GCAAATAAAT ATTTTCATTT TTATTTGTAA 1346
```

FIG.1B-3

```
ACGAATACAC CAAAAGGAGG CGCTCTTAAT AACTCCCAAT GTAAAAAGTT TTGTTTTAAT 1406

AAAAAATTAA TTATTATTCT TGCCAACAAA TGGCTAGAAA GGACTGAATA GATTATATAT 1466

TGCCAGATGT TAATACTGTA ACATACTTTT TAAATAACAT ATTTCTTAAA TCCAAATTTC 1526

TCTCAATGTT AGATTTAATT CCCTCAATAA CACCAATGTT TTGTTTTGTT TCGTTCTGGG 1586

TCATAAAACT TTGTTAAGGA ACTCTTTTGG AATAAAGAGC AGGATGCTGC GGAATTC    1643
```

FIG.1B-4

GAATTCCGCA GCC ATG ACC CCG CAG CTT CTC CTG GCC CTT GTC CTC TGG   49

Met Thr Pro Gln Leu Leu Leu Ala Leu Val Leu Trp
            1         5              10

GCC AGC TGC CCG CCC TGC AGT GGA AGG AAA GGG CCC CCA GCA GCT CTG   97

Ala Ser Cys Pro Pro Cys Ser Gly Arg Lys Gly Pro Pro Ala Ala Leu
     15             20             25

ACA CTG CCC CGG GTG CAA TGC CGA GCC TCT CGG TAC CCG ATC GCC GTG  145

Thr Leu Pro Arg Val Gln Cys Arg Ala Ser Arg Tyr Pro Ile Ala Val
     30             35             40

GAT TGC TCC TGG ACC CTG CCG CCT GCT CCA AAC TCC ACC AGC CCC GTG  193

Asp Cys Ser Trp Thr Leu Pro Pro Ala Pro Asn Ser Thr Ser Pro Val
     45             50         CHO ### ###      60
                                      55

TCC TTC ATT GCC ACG TAC AGG CTC GGC ATG GCT GCC CGG GGC CAC AGC  241

Ser Phe Ile Ala Thr Tyr Arg Leu Gly Met Ala Ala Arg Gly His Ser
              65                70              75

TGG CCC TGC CTG CAG CAG ACG CCA ACG TCC ACC AGC TGC ACC ATC AGC  289

Trp Pro Cys Leu Gln Gln Thr Pro Thr Ser Thr Ser Cys Thr Ile Thr
              80                85              90

GAT GTC CAG CTG TTC TCC ATG GCT CCC TAC GTG CTC AAT GTC ACC GCC  337

Asp Val Gln Leu Phe Ser Met Ala Pro Tyr Val Leu Asn Val Thr Ala
     95             100            105 CHO ### ###

GTC CAC CCC TGG GGC TCC AGC AGC AGC TTC GTG CCT TTC ATA ACA GAG  385

Val His Pro Trp Gly Ser Ser Ser Ser Phe Val Pro Phe Ile Thr Glu
    110             115             120

CAC ATC ATC AAG CCC GAC CCT CCA GAA GGC GTG CGC CTA AGC CCC CTC  433

His Ile Ile Lys Pro Asp Pro Pro Glu Gly Val Arg Leu Ser Pro Leu
125              130             135            140

FIG.5A

| | |
|---|---|
| GCT GAG CGC CAG CTA CAG GTG CAG TGG GAG CCT CCC GGG TCC TGG CCC | 481 |

Ala Glu Arg Gln Leu Gln Val Gln Trp Glu Pro Pro Gly Ser Trp Pro
              145              150              155

| | |
|---|---|
| TTC CCA GAG ATC TTC TCA CTG AAG TAC TGG ATC CGT TAC AAG CGT CAG | 529 |

Phe Pro Glu Ile Phe Ser Leu Lys Tyr Trp Ile Arg Tyr Lys Arg Gln
        160              165             170

| | |
|---|---|
| GGA GCT GCG CGC TTC CAC CGG GTG GGG CCC ATT GAA GCC ACG TCC TTC | 577 |

Gly Ala Ala Arg Phe His Arg Val Gly Pro Ile Glu Ala Thr Ser Phe
          175              180           185

| | |
|---|---|
| ATC CTC AGG GCT GTG CGG CCC CGA GCC AGG TAC TAC GTC CAA GTG GCG | 625 |

Ile Leu Arg Ala Val Arg Pro Arg Ala Arg Tyr Tyr Val Gln Val Ala
        190              195           200

| | |
|---|---|
| GCT CAG GAC CTC ACA GAC TAC GGG GAA CTG AGT GAC TGG AGT CTC CCC | 673 |

Ala Gln Asp Leu Thr Asp Tyr Gly Glu Leu Ser Asp Trp Ser Leu Pro
205           210             215           220

| | |
|---|---|
| GCC ACT GCC ACA ATG AGC CTG GGC AAG TAGCAAGGGC TTCCCGCTGC | 720 |

Ala Thr Ala Thr Met Ser Leu Gly Lys ***
              225

| | |
|---|---|
| CTCCAGACAG CACCTGGGTC CTCGCCACCC TAAGCCCCGG GACACCTGTT GGAGGGCGGA | 780 |
| TGGGATCTGC CTAGCCTGGG CTGGAGTCCT TGCTTTGCTG CTGCTGAGCT GCCGGGCAAC | 840 |
| CTCAGATGAC CGACTTTTCC CTTTGAGCCT CAGTTTCTCT AGCTGAGAAA TGGAGATGTA | 900 |
| CTACTCTCTC CTTTACCTTT ACCTTTACCA CAGTGCAGGG CTGACTGAAC TGTCACTGTG | 960 |

FIG.5B

```
AGATATTTTT TATTGTTTAA TTAGAAAAGA ATTGTTGTTG GGCTGGGCGC AGTGGATCGC  1020

ACCTGTAATC CCAGTCACTG GGAAGCCGAC GTGGGTGGGT AGCTTGAGGC CAGGAGCTCG  1080

AAACCAGTCC GGGCCACACA GCAAGACCCC ATCTCTAAAA AATTAATATA AATATAAAAT  1140

AAAAAAAAAA AAAAGGAATT C                                           1161
```

FIG.5C

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
   ( A ) LENGTH: 2154 base pairs
   ( B ) TYPE: nucleic acid
   ( C ) STRANDEDNESS: both
   ( D ) TOPOLOGY: linear ( i x ) FEATURE:
   ( A ) NAME/KEY: CDS
   ( B ) LOCATION: 64..1197

( x i ) SEQUENCE DESCRIPTION: SEQ ID NO:1:

```
GGAATTCCGT AGTGCGAGGC CGGGCACAGC CTTCCTGTGT GGTTTTACCG CCCAGAGAGC            60

GTC ATG GAC CTG GGG AAA CCA ATG AAA AGC GTG CTG GTG GTG GCT CTC            108
    Met Asp Leu Gly Lys Pro Met Lys Ser Val Leu Val Val Ala Leu
    1               5                  10                  15

CTT GTC ATT TTC CAG GTA TGC CTG TGT CAA GAT GAG GTC ACG GAC GAT            156
Leu Val Ile Phe Gln Val Cys Leu Cys Gln Asp Glu Val Thr Asp Asp
                20                  25                  30

TAC ATC GGA GAC AAC ACC ACA GTG GAC TAC ACT TTG TTC GAG TCT TTG            204
Tyr Ile Gly Asp Asn Thr Thr Val Asp Tyr Thr Leu Phe Glu Ser Leu
            35                  40                  45

TGC TCC AAG AAG GAC GTG CGG AAC TTT AAA GCC TGG TTC CTC CCT ATC            252
Cys Ser Lys Lys Asp Val Arg Asn Phe Lys Ala Trp Phe Leu Pro Ile
        50                  55                  60

ATG TAC TCC ATC ATT TGT TTC GTG GGC CTA CTG GGC AAT GGG CTG GTC            300
Met Tyr Ser Ile Ile Cys Phe Val Gly Leu Leu Gly Asn Gly Leu Val
    65                  70                  75

GTG TTG ACC TAT ATC TAT TTC AAG AGG CTC AAG ACC ATG ACC GAT ACC            348
Val Leu Thr Tyr Ile Tyr Phe Lys Arg Leu Lys Thr Met Thr Asp Thr
80                  85                  90                  95

TAC CTG CTC AAC CTG GCG GTG GCA GAC ATC CTC TTC CTC CTG ACC CTT            396
Tyr Leu Leu Asn Leu Ala Val Ala Asp Ile Leu Phe Leu Leu Thr Leu
                100                 105                 110

CCC TTC TGG GCC TAC AGC GCG GCC AAG TCC TGG GTC TTC GGT GTC CAC            444
Pro Phe Trp Ala Tyr Ser Ala Ala Lys Ser Trp Val Phe Gly Val His
            115                 120                 125

TTT TGC AAG CTC ATC TTT GCC ATC TAC AAG ATG AGC TTC TTC AGT GGC            492
Phe Cys Lys Leu Ile Phe Ala Ile Tyr Lys Met Ser Phe Phe Ser Gly
        130                 135                 140

ATG CTC CTA CTT CTT TGC ATC AGC ATT GAC CGC TAC GTG GCC ATC GTC            540
Met Leu Leu Leu Leu Cys Ile Ser Ile Asp Arg Tyr Val Ala Ile Val
    145                 150                 155

CAG GCT GTC TCA GCT CAC CGC CAC CGT GCC CGC GTC CTT CTC ATC AGC            588
Gln Ala Val Ser Ala His Arg His Arg Ala Arg Val Leu Leu Ile Ser
160                 165                 170                 175

AAG CTG TCC TGT GTG GGC AGC GCC ATA CTA GCC ACA GTG CTC TCC ATC            636
Lys Leu Ser Cys Val Gly Ser Ala Ile Leu Ala Thr Val Leu Ser Ile
                180                 185                 190

CCA GAG CTC CTG TAC AGT GAC CTC CAG AGG AGC AGC AGT GAG CAA GCG            684
Pro Glu Leu Leu Tyr Ser Asp Leu Gln Arg Ser Ser Ser Glu Gln Ala
            195                 200                 205

ATG CGA TGC TCT CTC ATC ACA GAG CAT GTG GAG GCC TTT ATC ACC ATC            732
Met Arg Cys Ser Leu Ile Thr Glu His Val Glu Ala Phe Ile Thr Ile
        210                 215                 220

CAG GTG GCC CAG ATG GTG ATC GGC TTT CTG GTC CCC CTG CTG GCC ATG            780
Gln Val Ala Gln Met Val Ile Gly Phe Leu Val Pro Leu Leu Ala Met
    225                 230                 235

AGC TTC TGT TAC CTT GTC ATC ATC CGC ACC CTG CTC CAG GCA CGC AAC            828
Ser Phe Cys Tyr Leu Val Ile Ile Arg Thr Leu Leu Gln Ala Arg Asn
240                 245                 250                 255

TTT GAG CGC AAC AAG GCC ATC AAG GTG ATC ATC GCT GTG GTC GTG GTC            876
```

| | | | | | | | | | | | | | | |
|---|---|---|---|---|---|---|---|---|---|---|---|---|---|---|
| Phe | Glu | Arg | Asn | Lys 260 | Ala | Ile | Lys | Val | Ile 265 | Ile | Ala | Val | Val 270 | Val |

| | | | | | | | | | | | | | | | |
|---|---|---|---|---|---|---|---|---|---|---|---|---|---|---|---|
| TTC | ATA | GTC | TTC | CAG | CTG | CCC | TAC | AAT | GGG | GTG | GTC | CTG | GCC | CAG | ACG |
| Phe | Ile | Val | Phe 275 | Gln | Leu | Pro | Tyr | Asn 280 | Gly | Val | Val | Leu | Ala 285 | Gln | Thr |

924

| GTG | GCC | AAC | TTC | AAC | ATC | ACC | AGT | AGC | ACC | TGT | GAG | CTC | AGT | AAG | CAA |
|---|---|---|---|---|---|---|---|---|---|---|---|---|---|---|---|
| Val | Ala | Asn 290 | Phe | Asn | Ile | Thr | Ser 295 | Ser | Thr | Cys | Glu | Leu 300 | Ser | Lys | Gln |

972

| CTC | AAC | ATC | GCC | TAC | GAC | GTC | ACC | TAC | AGC | CTG | GCC | TGC | GTC | CGC | TGC |
|---|---|---|---|---|---|---|---|---|---|---|---|---|---|---|---|
| Leu | Asn 305 | Ile | Ala | Tyr | Asp 310 | Val | Thr | Tyr | Ser | Leu 315 | Ala | Cys | Val | Arg | Cys |

1020

| TGC | GTC | AAC | CCT | TTC | TTG | TAC | GCC | TTC | ATC | GGC | GTC | AAG | TTC | CGC | AAC |
|---|---|---|---|---|---|---|---|---|---|---|---|---|---|---|---|
| Cys 320 | Val | Asn | Pro | Phe | Leu 325 | Tyr | Ala | Phe | Ile | Gly 330 | Val | Lys | Phe | Arg | Asn 335 |

1068

| GAT | ATC | TTC | AAG | CTC | TTC | AAG | GAC | CTG | GGC | TGC | CTC | AGC | CAG | GAG | CAG |
|---|---|---|---|---|---|---|---|---|---|---|---|---|---|---|---|
| Asp | Ile | Phe | Lys | Leu 340 | Phe | Lys | Asp | Leu | Gly 345 | Cys | Leu | Ser | Gln | Glu 350 | Gln |

1116

| CTC | CGG | CAG | TGG | TCT | TCC | TGT | CGG | CAC | ATC | CGG | CGC | TCC | TCC | ATG | AGT |
|---|---|---|---|---|---|---|---|---|---|---|---|---|---|---|---|
| Leu | Arg | Gln | Trp 355 | Ser | Ser | Cys | Arg | His 360 | Ile | Arg | Arg | Ser | Ser 365 | Met | Ser |

1164

| GTG | GAG | GCC | GAG | ACC | ACC | ACC | ACC | TTC | TCC | CCA | TAGGCGACTC | TTCTGCCTGG |
|---|---|---|---|---|---|---|---|---|---|---|---|---|
| Val | Glu | Ala | Glu 370 | Thr | Thr | Thr | Thr | Phe 375 | Ser | Pro | | |

1217

| | | | | | |
|---|---|---|---|---|---|
| ACTAGAGGGA | CCTCTCCCAG | GGTCCCTGGG | GTGGGGATAG | GGAGCAGATG | CAATGACTCA | 1277
| GGACATCCCC | CCGCCAAAAG | CTGCTCAGGG | GAAAAAGCAG | CTCTCCCCTC | AGAGTGCAAG | 1337
| CCCCTGCTCC | AGAAGATAGC | TTCACCCCAA | TCCCAGCTAC | CTCAACCAAT | GCCAAAAAAA | 1397
| GACAGGGCTG | ATAAGCTAAC | ACCAGACAGA | CAACACTGGG | AAACAGAGGC | TATTGTCCCC | 1457
| TAAACCAAAA | ACTGAAAGTG | AAAGTCCAGA | AACTGTTCCC | ACCTGCTGGA | GTGAAGGGGC | 1517
| CAAGGAGGGT | GAGTGCAAGG | GGCGTGGGAG | TGGCCTGAAG | AGTCCTCTGA | ATGAACCTTC | 1577
| TGGCCTCCCA | CAGACTCAAA | TGCTCAGACC | AGCTCTTCCG | AAAACCAGGC | CTTATCTCCA | 1637
| AGACCAGAGA | TAGTGGGGAG | ACTTCTTGGC | TTGGTGAGGA | AAAGCGGACA | TCAGCTGGTC | 1697
| AAACAAACTC | TCTGAACCCC | TCCCTCCATC | GTTTCTTCA | CTGTCCTCCA | AGCCAGCGGG | 1757
| AATGGCAGCT | GCCACGCCGC | CCTAAAAGCA | CACTCATCCC | CTCACTTGCC | GCGTCGCCCT | 1817
| CCCAGGCTCT | CAACAGGGGA | GAGTGTGGTG | TTTCCTGCAG | GCCAGGCCAG | CTGCCTCCGC | 1877
| GTGATCAAAG | CCACACTCTG | GGCTCCAGAG | TGGGGATGAC | ATGCACTCAG | CTCTTGGCTC | 1937
| CACTGGGATG | GGAGGAGAGG | ACAAGGGAAA | TGTCAGGGGC | GGGGAGGGTG | ACAGTGGCCG | 1997
| CCCAAGGCCA | CGAGCTTGTT | CTTTGTTCTT | TGTCACAGGG | ACTGAAAACC | TCTCCTCATG | 2057
| TTCTGCTTTC | GATTCGTTAA | GAGAGCAACA | TTTTACCCAC | ACACAGATAA | AGTTTTCCCT | 2117
| TGAGGAAACA | ACAGCTTTAA | AAAAAAAAAA | GGAATTC | | | 2154

( 2 ) INFORMATION FOR SEQ ID NO:2:

( i ) SEQUENCE CHARACTERISTICS:
        ( A ) LENGTH: 378 amino acids
        ( B ) TYPE: amino acid
        ( D ) TOPOLOGY: linear ( x i ) SEQUENCE DESCRIPTION: SEQ ID NO:2:

| Met 1 | Asp | Leu | Gly | Lys 5 | Pro | Met | Lys | Ser | Val 10 | Leu | Val | Val | Ala | Leu 15 | Leu |
|---|---|---|---|---|---|---|---|---|---|---|---|---|---|---|---|
| Val | Ile | Phe | Gln 20 | Val | Cys | Leu | Cys | Gln 25 | Asp | Glu | Val | Thr | Asp 30 | Asp | Tyr |
| Ile | Gly | Asp | Asn | Thr | Thr | Val | Asp | Tyr | Thr | Leu | Phe | Glu | Ser | Leu | Cys |

|  | 35 |  |  |  |  | 40 |  |  |  |  | 45 |  |  |  |
|---|---|---|---|---|---|---|---|---|---|---|---|---|---|---|
| Ser | Lys 50 | Lys | Asp | Val | Arg | Asn 55 | Phe | Lys | Ala | Trp | Phe 60 | Leu | Pro | Ile | Met |
| Tyr 65 | Ser | Ile | Ile | Cys | Phe 70 | Val | Gly | Leu | Leu | Gly 75 | Asn | Gly | Leu | Val | Val 80 |
| Leu | Thr | Tyr | Ile | Tyr 85 | Phe | Lys | Arg | Leu | Lys 90 | Thr | Met | Thr | Asp | Thr 95 | Tyr |
| Leu | Leu | Asn | Leu 100 | Ala | Val | Ala | Asp | Ile 105 | Leu | Phe | Leu | Leu | Thr 110 | Leu | Pro |
| Phe | Trp | Ala 115 | Tyr | Ser | Ala | Ala | Lys 120 | Ser | Trp | Val | Phe | Gly 125 | Val | His | Phe |
| Cys | Lys 130 | Leu | Ile | Phe | Ala | Ile 135 | Tyr | Lys | Met | Ser | Phe 140 | Phe | Ser | Gly | Met |
| Leu 145 | Leu | Leu | Leu | Cys | Ile 150 | Ser | Ile | Asp | Arg | Tyr 155 | Val | Ala | Ile | Val | Gln 160 |
| Ala | Val | Ser | Ala | His 165 | Arg | His | Arg | Ala | Arg 170 | Val | Leu | Leu | Ile | Ser 175 | Lys |
| Leu | Ser | Cys | Val 180 | Gly | Ser | Ala | Ile | Leu 185 | Ala | Thr | Val | Leu | Ser 190 | Ile | Pro |
| Glu | Leu | Leu 195 | Tyr | Ser | Asp | Leu | Gln 200 | Arg | Ser | Ser | Ser | Glu 205 | Gln | Ala | Met |
| Arg | Cys 210 | Ser | Leu | Ile | Thr | Glu 215 | His | Val | Glu | Ala | Phe 220 | Ile | Thr | Ile | Gln |
| Val 225 | Ala | Gln | Met | Val | Ile 230 | Gly | Phe | Leu | Val | Pro 235 | Leu | Leu | Ala | Met | Ser 240 |
| Phe | Cys | Tyr | Leu | Val 245 | Ile | Ile | Arg | Thr | Leu 250 | Leu | Gln | Ala | Arg | Asn 255 | Phe |
| Glu | Arg | Asn | Lys 260 | Ala | Ile | Lys | Val | Ile 265 | Ile | Ala | Val | Val | Val 270 | Val | Phe |
| Ile | Val | Phe 275 | Gln | Leu | Pro | Tyr | Asn 280 | Gly | Val | Val | Leu | Ala 285 | Gln | Thr | Val |
| Ala | Asn 290 | Phe | Asn | Ile | Thr | Ser 295 | Ser | Thr | Cys | Glu | Leu 300 | Ser | Lys | Gln | Leu |
| Asn 305 | Ile | Ala | Tyr | Asp | Val 310 | Thr | Tyr | Ser | Leu | Ala 315 | Cys | Val | Arg | Cys | Cys 320 |
| Val | Asn | Pro | Phe | Leu 325 | Tyr | Ala | Phe | Ile | Gly 330 | Val | Lys | Phe | Arg | Asn 335 | Asp |
| Ile | Phe | Lys | Leu 340 | Phe | Lys | Asp | Leu | Gly 345 | Cys | Leu | Ser | Gln | Glu 350 | Gln | Leu |
| Arg | Gln | Trp 355 | Ser | Ser | Cys | Arg | His 360 | Ile | Arg | Arg | Ser | Ser 365 | Met | Ser | Val |
| Glu | Ala 370 | Glu | Thr | Thr | Thr | Thr 375 | Phe | Ser | Pro |  |  |  |  |  |  |

( 2 ) INFORMATION FOR SEQ ID NO:3:

( i ) SEQUENCE CHARACTERISTICS:
        ( A ) LENGTH: 1643 base pairs
        ( B ) TYPE: nucleic acid
        ( C ) STRANDEDNESS: both
        ( D ) TOPOLOGY: linear ( i x ) FEATURE:
        ( A ) NAME/KEY: CDS
        ( B ) LOCATION: 34..1116

( x i ) SEQUENCE DESCRIPTION: SEQ ID NO:3:

-continued

```
GGAATTCCCT GATATACACC TGGACCACCA CCA ATG GAT ATA CAA ATG GCA AAC     54
                                   Met Asp Ile Gln Met Ala Asn
                                    1               5

AAT TTT ACT CCG CCC TCT GCA ACT CCT CAG GGA AAT GAC TGT GAC CTC    102
Asn Phe Thr Pro Pro Ser Ala Thr Pro Gln Gly Asn Asp Cys Asp Leu
            10              15                  20

TAT GCA CAT CAC AGC ACG GCC AGG ATA GTA ATG CCT CTG CAT TAC AGC    150
Tyr Ala His His Ser Thr Ala Arg Ile Val Met Pro Leu His Tyr Ser
        25              30              35

CTC GTC TTC ATC ATT GGG CTC GTG GGA AAC TTA CTA GCC TTG GTC GTC    198
Leu Val Phe Ile Ile Gly Leu Val Gly Asn Leu Leu Ala Leu Val Val
 40              45              50                          55

ATT GTT CAA AAC AGG AAA AAA ATC AAC TCT ACC ACC CTC TAT TCA ACA    246
Ile Val Gln Asn Arg Lys Lys Ile Asn Ser Thr Thr Leu Tyr Ser Thr
                 60              65                  70

AAT TTG GTG ATT TCT GAT ATA CTT TTT ACC ACG GCT TTG CCT ACA CGA    294
Asn Leu Val Ile Ser Asp Ile Leu Phe Thr Thr Ala Leu Pro Thr Arg
             75              80              85

ATA GCC TAC TAT GCA ATG GGC TTT GAC TGG AGA ATC GGA GAT GCC TTG    342
Ile Ala Tyr Tyr Ala Met Gly Phe Asp Trp Arg Ile Gly Asp Ala Leu
         90              95                 100

TGT AGG ATA ACT GCG CTA GTG TTT TAC ATC AAC ACA TAT GCA GGT GTG    390
Cys Arg Ile Thr Ala Leu Val Phe Tyr Ile Asn Thr Tyr Ala Gly Val
    105             110             115

AAC TTT ATG ACC TGC CTG AGT ATT GAC CGC TTC ATT GCT GTG GTG CAC    438
Asn Phe Met Thr Cys Leu Ser Ile Asp Arg Phe Ile Ala Val Val His
120             125             130                         135

CCT CTA CGC TAC AAC AAG ATA AAA AGG ATT GAA CAT GCA AAA GGC GTG    486
Pro Leu Arg Tyr Asn Lys Ile Lys Arg Ile Glu His Ala Lys Gly Val
                140             145                 150

TGC ATA TTT GTC TGG ATT CTA GTA TTT GCT CAG ACA CTC CCA CTC CTC    534
Cys Ile Phe Val Trp Ile Leu Val Phe Ala Gln Thr Leu Pro Leu Leu
            155             160                 165

ATC AAC CCT ATG TCA AAG CAG GAG GCT GAA AGG ATT ACA TGC ATG GAG    582
Ile Asn Pro Met Ser Lys Gln Glu Ala Glu Arg Ile Thr Cys Met Glu
        170             175                 180

TAT CCA AAC TTT GAA GAA ACT AAA TCT CTT CCC TGG ATT CTG CTT GGG    630
Tyr Pro Asn Phe Glu Glu Thr Lys Ser Leu Pro Trp Ile Leu Leu Gly
185             190                 195

GCA TGT TTC ATA GGA TAT GTA CTT CCA CTT ATA ATC ATT CTC ATC TGC    678
Ala Cys Phe Ile Gly Tyr Val Leu Pro Leu Ile Ile Ile Leu Ile Cys
200             205                 210                     215

TAT TCT CAG ATC TGC TGC AAA CTC TTC AGA ACT GCC AAA CAA AAC CCA    726
Tyr Ser Gln Ile Cys Cys Lys Leu Phe Arg Thr Ala Lys Gln Asn Pro
                220             225                 230

CTC ACT GAG AAA TCT GGT GTA AAC AAA AAG GCT CTC AAC ACA ATT ATT    774
Leu Thr Glu Lys Ser Gly Val Asn Lys Lys Ala Leu Asn Thr Ile Ile
            235             240                 245

CTT ATT ATT GTT GTG TTT GTT CTC TGT TTC ACA CCT TAC CAT GTT GCA    822
Leu Ile Ile Val Val Phe Val Leu Cys Phe Thr Pro Tyr His Val Ala
        250             255                 260

ATT ATT CAA CAT ATG ATT AAG AAG CTT CGT TTC TCT AAT TTC CTG GAA    870
Ile Ile Gln His Met Ile Lys Lys Leu Arg Phe Ser Asn Phe Leu Glu
265             270                 275

TGT AGC CAA AGA CAT TCG TTC CAG ATT TCT CTG CAC TTT ACA GTA TGC    918
Cys Ser Gln Arg His Ser Phe Gln Ile Ser Leu His Phe Thr Val Cys
280             285                 290                     295

CTG ATG AAC TTC AAT TGC TGC ATG GAC CCT TTT ATC TAC TTC TTT GCA    966
Leu Met Asn Phe Asn Cys Cys Met Asp Pro Phe Ile Tyr Phe Phe Ala
                300             305                 310
```

-continued

| TGT | AAA | GGG | TAT | AAG | AGA | AAG | GTT | ATG | AGG | ATG | CTG | AAA | CGG | CAA | GTC | 1014 |
| Cys | Lys | Gly | Tyr | Lys | Arg | Lys | Val | Met | Arg | Met | Leu | Lys | Arg | Gln | Val | |
| | | | 315 | | | | 320 | | | | | 325 | | | | |

| AGT | GTA | TCG | ATT | TCT | AGT | GCT | GTG | AAG | TCA | GCC | CCT | GAA | GAA | AAT | TCA | 1062 |
| Ser | Val | Ser | Ile | Ser | Ser | Ala | Val | Lys | Ser | Ala | Pro | Glu | Glu | Asn | Ser | |
| | | 330 | | | | | 335 | | | | | 340 | | | | |

| CGT | GAA | ATG | ACA | GAA | ACG | CAG | ATG | ATG | ATA | CAT | TCC | AAG | TCT | TCA | AAT | 1110 |
| Arg | Glu | Met | Thr | Glu | Thr | Gln | Met | Met | Ile | His | Ser | Lys | Ser | Ser | Asn | |
| | 345 | | | | | 350 | | | | | 355 | | | | | |

| GGA | AAG | TGAAATGGAT | TGTATTTTGG | TTTATAGTGA | CGTAAACTGT | ATGACAAACT | 1166 |
| Gly | Lys | | | | | | |
| 360 | | | | | | | |

| TTGCAGGACT | TCCCTTATAA | AGCAAAATAA | TTGTTCAGCT | TCCAATTAGT | ATTCTTTTAT | 1226 |
| ATTTCTTTCA | TTGGGCGCTT | TCCCATCTCC | AACTCGGAAG | TAAGCCCAAG | AGAACAACAT | 1286 |
| AAAGCAAACA | ACATAAAGCA | CAATAAAAAT | GCAAATAAAT | ATTTTCATTT | TTATTTGTAA | 1346 |
| ACGAATACAC | CAAAAGGAGG | CGCTCTTAAT | AACTCCCAAT | GTAAAAAGTT | TTGTTTTAAT | 1406 |
| AAAAAATTAA | TTATTATTCT | TGCCAACAAA | TGGCTAGAAA | GGACTGAATA | GATTATATAT | 1466 |
| TGCCAGATGT | TAATACTGTA | ACATACTTTT | TAAATAACAT | ATTTCTTAAA | TCCAAATTTC | 1526 |
| TCTCAATGTT | AGATTTAATT | CCCTCAATAA | CACCAATGTT | TTGTTTTGTT | TCGTTCTGGG | 1586 |
| TCATAAAACT | TTGTTAAGGA | ACTCTTTTGG | AATAAAGAGC | AGGATGCTGC | GGAATTC | 1643 |

( 2 ) INFORMATION FOR SEQ ID NO:4:

( i ) SEQUENCE CHARACTERISTICS:
        ( A ) LENGTH: 361 amino acids
        ( B ) TYPE: amino acid
        ( D ) TOPOLOGY: linear ( x i ) SEQUENCE DESCRIPTION: SEQ ID NO:4:

| Met | Asp | Ile | Gln | Met | Ala | Asn | Asn | Phe | Thr | Pro | Pro | Ser | Ala | Thr | Pro |
| 1 | | | | 5 | | | | | 10 | | | | | 15 | |

| Gln | Gly | Asn | Asp | Cys | Asp | Leu | Tyr | Ala | His | His | Ser | Thr | Ala | Arg | Ile |
| | | | 20 | | | | | 25 | | | | | 30 | | |

| Val | Met | Pro | Leu | His | Tyr | Ser | Leu | Val | Phe | Ile | Ile | Gly | Leu | Val | Gly |
| | | 35 | | | | | 40 | | | | | 45 | | | |

| Asn | Leu | Leu | Ala | Leu | Val | Val | Ile | Val | Gln | Asn | Arg | Lys | Lys | Ile | Asn |
| | 50 | | | | | 55 | | | | | 60 | | | | |

| Ser | Thr | Thr | Leu | Tyr | Ser | Thr | Asn | Leu | Val | Ile | Ser | Asp | Ile | Leu | Phe |
| 65 | | | | | 70 | | | | | 75 | | | | | 80 |

| Thr | Thr | Ala | Leu | Pro | Thr | Arg | Ile | Ala | Tyr | Tyr | Ala | Met | Gly | Phe | Asp |
| | | | | 85 | | | | | 90 | | | | | 95 | |

| Trp | Arg | Ile | Gly | Asp | Ala | Leu | Cys | Arg | Ile | Thr | Ala | Leu | Val | Phe | Tyr |
| | | | 100 | | | | | 105 | | | | | 110 | | |

| Ile | Asn | Thr | Tyr | Ala | Gly | Val | Asn | Phe | Met | Thr | Cys | Leu | Ser | Ile | Asp |
| | | 115 | | | | | 120 | | | | | 125 | | | |

| Arg | Phe | Ile | Ala | Val | Val | His | Pro | Leu | Arg | Tyr | Asn | Lys | Ile | Lys | Arg |
| | 130 | | | | | 135 | | | | | 140 | | | | |

| Ile | Glu | His | Ala | Lys | Gly | Val | Cys | Ile | Phe | Val | Trp | Ile | Leu | Val | Phe |
| 145 | | | | | 150 | | | | | 155 | | | | | 160 |

| Ala | Gln | Thr | Leu | Pro | Leu | Leu | Ile | Asn | Pro | Met | Ser | Lys | Gln | Glu | Ala |
| | | | | 165 | | | | | 170 | | | | | 175 | |

| Glu | Arg | Ile | Thr | Cys | Met | Glu | Tyr | Pro | Asn | Phe | Glu | Glu | Thr | Lys | Ser |
| | | | 180 | | | | | 185 | | | | | 190 | | |

| Leu | Pro | Trp | Ile | Leu | Leu | Gly | Ala | Cys | Phe | Ile | Gly | Tyr | Val | Leu | Pro |
| | | | 195 | | | | | 200 | | | | | 205 | | |

| | | | | | | | | | | | | |
|---|---|---|---|---|---|---|---|---|---|---|---|---|
| Leu | Ile | Ile | Ile | Leu | Ile | Cys | Tyr | Ser | Gln | Ile | Cys | Cys | Lys | Leu | Phe |
| | 210 | | | | 215 | | | | | 220 | | | | | |
| Arg | Thr | Ala | Lys | Gln | Asn | Pro | Leu | Thr | Glu | Lys | Ser | Gly | Val | Asn | Lys |
| 225 | | | | | 230 | | | | | 235 | | | | | 240 |
| Lys | Ala | Leu | Asn | Thr | Ile | Ile | Leu | Ile | Ile | Val | Val | Phe | Val | Leu | Cys |
| | | | | 245 | | | | | 250 | | | | | 255 | |
| Phe | Thr | Pro | Tyr | His | Val | Ala | Ile | Ile | Gln | His | Met | Ile | Lys | Lys | Leu |
| | | | 260 | | | | | 265 | | | | | 270 | | |
| Arg | Phe | Ser | Asn | Phe | Leu | Glu | Cys | Ser | Gln | Arg | His | Ser | Phe | Gln | Ile |
| | | 275 | | | | | 280 | | | | | 285 | | | |
| Ser | Leu | His | Phe | Thr | Val | Cys | Leu | Met | Asn | Phe | Asn | Cys | Cys | Met | Asp |
| | 290 | | | | | 295 | | | | | 300 | | | | |
| Pro | Phe | Ile | Tyr | Phe | Phe | Ala | Cys | Lys | Gly | Tyr | Lys | Arg | Lys | Val | Met |
| 305 | | | | | 310 | | | | | 315 | | | | | 320 |
| Arg | Met | Leu | Lys | Arg | Gln | Val | Ser | Val | Ser | Ile | Ser | Ser | Ala | Val | Lys |
| | | | | 325 | | | | | 330 | | | | | 335 | |
| Ser | Ala | Pro | Glu | Glu | Asn | Ser | Arg | Glu | Met | Thr | Glu | Thr | Gln | Met | Met |
| | | | 340 | | | | | 345 | | | | | 350 | | |
| Ile | His | Ser | Lys | Ser | Ser | Asn | Gly | Lys | | | | | | | |
| | | 355 | | | | | 360 | | | | | | | | |

( 2 ) INFORMATION FOR SEQ ID NO:5:

( i ) SEQUENCE CHARACTERISTICS:
        ( A ) LENGTH: 1161 base pairs
        ( B ) TYPE: nucleic acid
        ( C ) STRANDEDNESS: both
        ( D ) TOPOLOGY: linear ( i x ) FEATURE:
        ( A ) NAME/KEY: CDS
        ( B ) LOCATION: 14..700

( x i ) SEQUENCE DESCRIPTION: SEQ ID NO:5:

```
GAATTCCGCA GCC ATG ACC CCG CAG CTT CTC CTG GCC CTT GTC CTC TGG         49
           Met Thr Pro Gln Leu Leu Leu Ala Leu Val Leu Trp
           1               5                   10

GCC AGC TGC CCG CCC TGC AGT GGA AGG AAA GGG CCC CCA GCA GCT CTG        97
Ala Ser Cys Pro Pro Cys Ser Gly Arg Lys Gly Pro Pro Ala Ala Leu
        15                  20                  25

ACA CTG CCC CGG GTG CAA TGC CGA GCC TCT CGG TAC CCG ATC GCC GTG        145
Thr Leu Pro Arg Val Gln Cys Arg Ala Ser Arg Tyr Pro Ile Ala Val
        30                  35                  40

GAT TGC TCC TGG ACC CTG CCG CCT GCT CCA AAC TCC ACC AGC CCC GTG        193
Asp Cys Ser Trp Thr Leu Pro Pro Ala Pro Asn Ser Thr Ser Pro Val
45                  50                  55                  60

TCC TTC ATT GCC ACG TAC AGG CTC GGC ATG GCT GCC CGG GGC CAC AGC        241
Ser Phe Ile Ala Thr Tyr Arg Leu Gly Met Ala Ala Arg Gly His Ser
                65                  70                  75

TGG CCC TGC CTG CAG CAG ACG CCA ACG TCC ACC AGC TGC ACC ATC ACG        289
Trp Pro Cys Leu Gln Gln Thr Pro Thr Ser Thr Ser Cys Thr Ile Thr
        80                  85                  90

GAT GTC CAG CTG TTC TCC ATG GCT CCC TAC GTG CTC AAT GTC ACC GCC        337
Asp Val Gln Leu Phe Ser Met Ala Pro Tyr Val Leu Asn Val Thr Ala
        95                  100                 105

GTC CAC CCC TGG GGC TCC AGC AGC AGC TTC GTG CCT TTC ATA ACA GAG        385
Val His Pro Trp Gly Ser Ser Ser Ser Phe Val Pro Phe Ile Thr Glu
        110                 115                 120

CAC ATC ATC AAG CCC GAC CCT CCA GAA GGC GTG CGC CTA AGC CCC CTC        433
His Ile Ile Lys Pro Asp Pro Pro Glu Gly Val Arg Leu Ser Pro Leu
```

|  | 125 |  |  |  | 130 |  |  |  | 135 |  |  |  | 140 |  |  |  |
|---|---|---|---|---|---|---|---|---|---|---|---|---|---|---|---|---|
| GCT | GAG | CGC | CAC | GTA | CAG | GTG | CAG | TGG | GAG | CCT | CCC | GGG | TCC | TGG | CCC | 481 |
| Ala | Glu | Arg | His | Val | Gln | Val | Gln | Trp | Glu | Pro | Pro | Gly | Ser | Trp | Pro |  |
|  |  |  |  | 145 |  |  |  |  | 150 |  |  |  |  | 155 |  |  |
| TTC | CCA | GAG | ATC | TTC | TCA | CTG | AAG | TAC | TGG | ATC | CGT | TAC | AAG | CGT | CAG | 529 |
| Phe | Pro | Glu | Ile | Phe | Ser | Leu | Lys | Tyr | Trp | Ile | Arg | Tyr | Lys | Arg | Gln |  |
|  |  |  | 160 |  |  |  |  | 165 |  |  |  |  | 170 |  |  |  |
| GGA | GCT | GCG | CGC | TTC | CAC | CGG | GTG | GGG | CCC | ATT | GAA | GCC | ACG | TCC | TTC | 577 |
| Gly | Ala | Ala | Arg | Phe | His | Arg | Val | Gly | Pro | Ile | Glu | Ala | Thr | Ser | Phe |  |
|  |  | 175 |  |  |  |  | 180 |  |  |  |  | 185 |  |  |  |  |
| ATC | CTC | AGG | GCT | GTG | CGG | CCC | CGA | GCC | AGG | TAC | TAC | GTC | CAA | GTG | GCG | 625 |
| Ile | Leu | Arg | Ala | Val | Arg | Pro | Arg | Ala | Arg | Tyr | Tyr | Val | Gln | Val | Ala |  |
|  |  | 190 |  |  |  |  | 195 |  |  |  |  | 200 |  |  |  |  |
| GCT | CAG | GAC | CTC | ACA | GAC | TAC | GGG | GAA | CTG | AGT | GAC | TGG | AGT | CTC | CCC | 673 |
| Ala | Gln | Asp | Leu | Thr | Asp | Tyr | Gly | Glu | Leu | Ser | Asp | Trp | Ser | Leu | Pro |  |
| 205 |  |  |  |  | 210 |  |  |  |  | 215 |  |  |  |  | 220 |  |
| GCC | ACT | GCC | ACA | ATG | AGC | CTG | GGC | AAG | TAGCAAGGGC | TTCCCGCTGC |  |  |  |  |  | 720 |
| Ala | Thr | Ala | Thr | Met | Ser | Leu | Gly | Lys |  |  |  |  |  |  |  |  |
|  |  |  |  | 225 |  |  |  |  |  |  |  |  |  |  |  |  |

```
CTCCAGACAG CACCTGGGTC CTCGCCACCC TAAGCCCCGG GACACCTGTT GGAGGGCGGA    780
TGGGATCTGC CTAGCCTGGG CTGGAGTCCT TGCTTTGCTG CTGCTGAGCT GCCGGGCAAC    840
CTCAGATGAC CGACTTTTCC CTTTGAGCCT CAGTTTCTCT AGCTGAGAAA TGGAGATGTA    900
CTACTCTCTC CTTTACCTTT ACCTTTACCA CAGTGCAGGG CTGACTGAAC TGTCACTGTG    960
AGATATTTTT TATTGTTTAA TTAGAAAAGA ATTGTTGTTG GGCTGGGCGC AGTGGATCGC   1020
ACCTGTAATC CCAGTCACTG GGAAGCCGAC GTGGGTGGGT AGCTTGAGGC CAGGAGCTCG   1080
AAACCAGTCC GGGCCACACA GCAAGACCCC ATCTCTAAAA AATTAATATA AATATAAAAT   1140
AAAAAAAAAA AAAAGGAATT C                                             1161
```

( 2 ) INFORMATION FOR SEQ ID NO:6:

( i ) SEQUENCE CHARACTERISTICS:
        ( A ) LENGTH: 229 amino acids
        ( B ) TYPE: amino acid
        ( D ) TOPOLOGY: linear ( x i ) SEQUENCE DESCRIPTION: SEQ ID NO:6:

```
Met Thr Pro Gln Leu Leu Leu Ala Leu Val Leu Trp Ala Ser Cys Pro
  1               5                  10                  15

Pro Cys Ser Gly Arg Lys Gly Pro Pro Ala Ala Leu Thr Leu Pro Arg
                 20                  25                  30

Val Gln Cys Arg Ala Ser Arg Tyr Pro Ile Ala Val Asp Cys Ser Trp
                 35                  40                  45

Thr Leu Pro Pro Ala Pro Asn Ser Thr Ser Pro Val Ser Phe Ile Ala
         50                  55                  60

Thr Tyr Arg Leu Gly Met Ala Ala Arg Gly His Ser Trp Pro Cys Leu
 65                  70                  75                  80

Gln Gln Thr Pro Thr Ser Thr Ser Cys Thr Ile Thr Asp Val Gln Leu
                 85                  90                  95

Phe Ser Met Ala Pro Tyr Val Leu Asn Val Thr Ala Val His Pro Trp
                100                 105                 110

Gly Ser Ser Ser Ser Phe Val Pro Phe Ile Thr Glu His Ile Ile Lys
                115                 120                 125

Pro Asp Pro Pro Glu Gly Val Arg Leu Ser Pro Leu Ala Glu Arg His
        130                 135                 140

Val Gln Val Gln Trp Glu Pro Pro Gly Ser Trp Pro Phe Pro Glu Ile
```

```
145                     150                     155                     160
Phe Ser Leu Lys Tyr Trp Ile Arg Tyr Lys Arg Gln Gly Ala Ala Arg
                165                 170                     175

Phe His Arg Val Gly Pro Ile Glu Ala Thr Ser Phe Ile Leu Arg Ala
            180                 185                 190

Val Arg Pro Arg Ala Arg Tyr Tyr Val Gln Val Ala Ala Gln Asp Leu
        195                 200                 205

Thr Asp Tyr Gly Glu Leu Ser Asp Trp Ser Leu Pro Ala Thr Ala Thr
    210                 215                 220

Met Ser Leu Gly Lys
225
```

( 2 ) INFORMATION FOR SEQ ID NO:7:

( i ) SEQUENCE CHARACTERISTICS:
        ( A ) LENGTH: 26 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:7:

ACTGAATTCG AGCTCCTGGC CTCAAG                    26

( 2 ) INFORMATION FOR SEQ ID NO:8:

( i ) SEQUENCE CHARACTERISTICS:
        ( A ) LENGTH: 26 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:8:

AAGGATCCCC AGCAGCTCTG ACACTG                    26

METHODS OF DETECTION OF EPSTEIN BARR VIRUS INDUCED GENES EXPRESSED IN THE PLACENTA

CROSS-REFERENCE TO RELATED APPLICANTS

This application is a continuation-in-part of U.S. Ser. No. 08/352,678, filed Nov. 30, 1994, which is a continuation of Ser. No. 07/980,518, filed Nov. 25, 1992, now abandoned the contents of which are incorporated herein by reference.

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

The present invention relates, in general, to Epstein Barr virus induced (EBI) genes. In particular, the present invention relates to DNA segments coding for EBI 1, EBI 2, or EBI 3 polypeptides; EBI 1, EBI 2, or EBI 3 polypeptides; recombinant DNA molecules; cells containing the recombinant DNA molecules; antisense EBI 1, EBI 2, or EBI 3 constructs; antibodies having binding affinity to an EBI 1, EBI 2, or EBI 3 polypeptide; hybridomas containing the antibodies; nucleic acid probes for the detection of the presence of Epstein Barr Virus; a method of detecting Epstein Barr virus in a sample; and kits containing nucleic acid probes or antibodies.

2. Related Art

Epstein-Barr Virus (EBV) is the cause of infectious mononucleosis, a benign proliferation of infected B lymphocytes (Henle, G., et al., *Proc. Natl. Acad. Sci. USA* 59(1):94–101 (1968)) and can also cause acute and rapidly progressive B lymphoproliferative disease in severely immune compromised patients or in experimental infection of tamarins (Miller, G., *Fields Virol.*, 2nd ed., 1921–58 (1990)). Infection of human B lymphocytes, in vitro, results in expression of six virus encoded nuclear proteins (EBNAs) and two virus encoded membrane proteins (LMPs) (Kieff and Liebowitz, *Fields Virol.*, 2nd ed., 1889–1920 (1990)), and in substantially altered cell growth (Nilsson and Klein, *Adv. Cancer Res.* 37(319):319–80 (1982)). EBV infected B lymphocytes recapitulate features of antigen stimulation in enlarging, increasing RNA synthesis, expressing activation antigens and adhesion molecules, secreting Ig and proliferating (Boyd, A. W., et al., *J. Immunol.* 134(3):1516–23 (1985); Gordon, J., et al., *Immunology* 58(4):591–5 (1986); Guy and Gordon, *Intl. J. Cancer* 43(4):703–8 (1989); Nilsson and Klein, *Adv. Cancer Res.* 37(319):319–80 (1982); Thorley-Lawson, D.A., et al., *J. Immunol.* 134(5):3007–12 (1985)). Unlike antigen stimulated B lymphocytes, EBV infected B lymphocytes continue to proliferate in vitro as immortalized lymphoblastoid cell lines (LCLs) (Nilsson, K., et al., *Intl. J. Cancer* 8(3):443–50 (1971)).

EBV effects on lymphocytes have been studied by comparing the properties of EBV-negative [EBV(−)] Burkitt lymphoma (BL) cell lines and EBV-positive [EBV(+)] derivatives, infected by EBV, in vitro (Calender, A., et al., *Proc. Natl. Acad. Sci. USA* 84(22):8060–4 (1987); Ehlin-Henriksson, B., et al., *Intl. J. Cancer* 39(2):211–8 (1987); Nilsson and Klein, *Adv. Cancer Res.* 37(319):319–80 (1982); Rowe, M., et al., *Intl. J. Cancer* 37(3):367–73 (1986)). EBV(−) BL cells resemble proliferating centroblasts of germinal centers, characteristically expressing CD10, CD20, CD77 (BLA), class II antigen, and the carbohydrate recognized by peanut agglutinin (Calender, A., et al., *Proc. Natl. Acad. Sci. USA* 84(22):8060–4 (1987); Ehlin-Henriksson, B., et al., *Intl. J. Cancer* 39(2):211–8 (1987); Favrot, M. C., et al., *Intl. J. Cancer* 38(6):901–6 (1986); Gregory, C. D., et al., *Intl. J. Cancer* 42(2):213–20 (1988); Gregory, C. D., et al., *J. Gen. Virol.* 71:1481–1495 (1990); Gregory, C. D., et al., *J. Immunol.* 139(1):313–8 (1987); Rowe, M., et al., *Intl. J. Cancer* 37(3):367–73 (1986); Rowe, M., et al., *Intl. J. Cancer* 35(4):435–41 (1985)). Both EBV(−) BL cells and centroblasts lack surface IgD and antigens associated with early phases of mitogen stimulation in vitro, including CD23, CD39 and CD30. In general, EBV(+) BL cells closely resemble EBV infected primary B lymphocytes in not expressing CD10 or CD77 and in expressing early activation and differentiation markers, vimentin, Bac-1, Bcl-2, surface IgD and CD44 (Calender, A., et al., *Proc. Natl. Acad. Sci. USA* 84(22):8060–4 (1987); Ehlin-Henriksson, B., et al., *Intl. J. Cancer* 39(2):211–8 (1987); Favrot, M. C., et al., *Intl. J. Cancer* 38(6):901–6 (1986); Gregory, C. D., et al., *J. Gen. Virol.* 71:1481–1495 (1990); Henderson, S., et al., *Cell* 65(7):1107–15 (1991); Rowe, M., et al., *Intl. J. Cancer* 37(3):367–73 (1986); Rowe, M., et al., *EMBO J.* 6(9):2743–51 (1987); Spira, G., et al., *J. Immunol.* 126(1):122–6 (1981); Suzuki, T., et al., *J. Immunol.* 137(4):1208–13 (1986)). Experiments with single gene transfer into EBV(−) B lymphoma cells, or with specifically mutated EBV recombinants reveal that EBNA 2, LMP 1 and EBNA 3C are essential for lymphocyte growth transformation and alter cellular or viral gene expression. Expression of EBNA 2 alone in EBV(−) BL cell lines results in enhanced transcription of CD23, CD21 (Cordier, M., et al., *J. Virol.* 64(3):1002–13 (1990); Wang, F., et al., *J. Virol.* 64(5):2309–18 (1990); Wang, F., et al., *Proc. Natl. Acad. Sci. USA* 84(10):3452–6 (1987)), and c-fgr (Knutson, J. C., *J. Virol.* 64(6):2530–6 (1990)). EBNA 2 also transactivates the LMP promoters (Fahraeus, R., et al., *Proc. Natl. Acad. Sci. USA* 87(19):7390–4 (1990); Wang, F., et al., *J. Virol.* 64(7):3407–16 (1990)). Analysis of a series of EBNA 2 mutants indicates that the ability of EBNA 2 to transactivate gene expression is tightly linked to its essential role in cell growth transformation (Cohen, J. I., et al., *J. Virol.* 65(5):2545–54 (1991)). LMP 1 is also critical to EBV's effects on cell growth. LMP 1 transforms immortalized rodent fibroblasts (Baichwal and Sugden, *Oncogene* 2(5):461–7 (1988); Wang, D., et al., *Cell* 43:831–40 (1985)) and induces vimentin, Bcl-2 and many of the activation markers and adhesion molecules that EBV induces in BL cells (Birkenbach, M., et al., *J. Virol.* 63(9):4079–84 (1989); Henderson, S., et al., *Cell* 65(7):1107–15 (1991); Wang, D., et al., *J. Virol.* 62(11):4173–84 (1988)). In EBV(−) BL cells, EBNA 3c induces higher level expression of CD21 (Wang, F., et al., *J. Virol.* 64(5):2309–18 (1990)).

Since altered B lymphocyte gene expression is a central theme in EBV induced changes in B lymphocyte growth, a more complete description of the repertoire of EBV induced genes would be advantageous prior to the investigation of specific genes for their role as mediators of EBV effects on cell growth. Also, because of the similar effects of EBV and antigen, EBV induced genes are likely to include mediators of antigen induced B lymphocyte growth or differentiation. Previously, recognition of such genes has been largely based on increased expression of lymphocyte surface markers (Calender, A., et al., *Proc. Natl. Acad. Sci. USA* 84(22)

:8060–4 (1987)), defined by monoclonal antibodies derived against EBV or antigen activated B lymphocytes. Few of these surface markers are likely candidates for important effectors of EBV or antigen induced alterations in lymphocyte growth. The experiments described here use subtractive hybridization to identify cDNA clones of RNAs which are more abundant in an in vitro infected EBV(+) BL cell than in the non-infected EBV(−) control BL cell.

SUMMARY OF THE INVENTION

It is a general object of this invention to provide EBI 1, EBI 2, and EBI 3 DNA segments. It is a specific object of this invention to provide a DNA segment coding for a polypeptide having an amino acid sequence corresponding to an EBI 1, EBI 2, or EBI 3 polypeptide.

It is another object of the invention to provide a substantially pure polypeptide having an amino acid sequence corresponding to an EBI 1, EBI 2, or EBI 3 polypeptide.

It is a further object of the invention to provide a nucleic acid probe for the detection of the presence of Epstein Barr Virus in a sample.

It is another object of the invention to provide a method of detecting Epstein Barr Virus in a sample.

It is a further object of the invention to provide a kit for identifying or amplifying a gene encoding an EBI 1, EBI 2, or EBI 3 polypeptide.

It is another object of the invention to provide a DNA molecule comprising, 5' to 3', a promoter effective to initiate transcription in a cell and an EBI 1, EBI 2, or EBI 3 DNA segment.

It is a further object of the invention to provide a recombinant DNA molecule comprising a vector and an EBI 1, EBI 2, or EBI 3 DNA segment.

It is a further object of the invention to provide a DNA molecule comprising a transcriptional region functional in a cell, a sequence complimentary to an RNA sequence encoding an amino acid sequence corresponding to an EBI 1, EBI 2, or EBI 3 polypeptide, and a transcriptional termination region functional in said cell.

It is another object of the invention to provide cells containing the above-described DNA molecules.

It is a further object of the invention to provide an antibody having binding affinity to an EBI 1, EBI 2, or EBI 3 polypeptide, or a binding fragment thereof.

It is another object of the invention to provide a hybridoma which produces the above-described antibody, or binding fragment thereof.

It is a further object of the invention to provide a method of detecting an EBI 1, EBI 2, or EBI 3 polypeptide in a sample.

It is another object of the invention to provide a diagnostic kit comprising EBI 1, EBI 2, or EBI 3 antibodies.

The invention further provides a method of determining a prognosis for a patient having a neoplastic disorder comprising:
  a) taking a tumor biopsy sample from the patient;
  b) evaluating the characteristics or presence of EBI-3 DNA, EBI-3 mRNA and/or EBI-3 protein in the biopsy sample to obtain a first set of results;
  c) comparing the first set of results from the evaluation of step "a" with a second set of results obtained using similar evaluations in an individual not suspected of having a neoplastic disorder; and
  d) determining the prognosis.

The invention also provides a method of diagnosing a tendency to develop a EBI-3-associated tumor comprising:
  a) taking a biological sample from the patient;
  b) evaluating the characteristics or presence of EBI-3 DNA, EBI-3 mRNA and/or EBI-3 protein in the biological sample to obtain a first set of results;
  c) comparing the first set of results from the evaluation of step "b" with a second set of results obtained using similar evaluations in an individual not suspected of having an EBI-3-associated tumor; and
  d) diagnosing the tendency of the individual to develop EBI-3-associated tumors when the first set of results and the second set of results differs.

The invention further provides a method of determining the prognosis of a patient with a neoplastic disorder comprising:
  a) incubating a biological sample from the patient which is suspected of containing EBI-3, in the presence of at least one binding molecule capable of identifying said EBI-3;
  b) detecting the binding molecule which is bound in said sample; and
  c) comparing the amount of EBI-3 bound with the amount bound in a biological sample from a patient without a neoplastic disorder; wherein detection of an increase of EBI-3 bound in the biological sample from a patient with a neoplastic disorder as compared to an amount of EBI-3 present in a patient without a neoplastic disorder indicates that the patient may respond to anti-EBI-3 agents. Preferably, the detection is by immunometric assay. More preferably, the immunometric assay is a monoclonal antibody-based immunometric assay.

The invention also provides a method of reducing cytotoxic T cell-mediated responses in a patient comprising administering a therapeutically effective amount of EBI-3 to the patient such that the cytotoxic T cell-mediated response is reduced. Preferably, the reduced cytotoxic T cell-mediated response inhibits allograft rejection. Preferably, the reduced cytotoxic T cell-mediated response inhibits graft-versus-host disease. More preferably, the reduced cytotoxic T cell-mediated response inhibits an autoimmune disorder (for example, arthritis).

The invention further provides a method of monitoring fetal or placental development by measuring levels of EBI 3 in maternal serum.

The invention further provides a method of progressing fetal development in utero comprising administering a therapeutically effective amount of EBI-3 to a pregnant patient such that the fetal development progresses.

The invention also provides a method of progressing placental development comprising administering a therapeutically effective amount of EBI-3 to a pregnant patient such that the placental development progresses.

Further objects and advantages of the present invention will be clear from the description that follows.

BRIEF DESCRIPTION OF THE FIGURES

FIG. 1A–B. EBV induced gene (EBI) A and B RNA: Nucleotide and deduced amino acid sequences. (A) 1–4 EBI 1 SEQ ID NO:1 has two potential translational initiation codons. In frame stop codons are indicated asterisks (*). A hydrophobic amino terminal segment (single underline) is predicted to be a signal peptide for membrane translocation. Seven other highly hydrophobic segments are predicted to form membrane spanning domains and are delineated by single underlines. Potential asparagine linked glycosylation sites (CHO######) are present in the extracellular amino terminal segment and third extracellular loop. The sequence motif S-(I/V)-D-R-(Y/F)-X-X-X-X (where X represents consecutive hydrophobic residues), is highly conserved among a large number of G-protein coupled receptors and is indicated at the end of the third transmembrane domain (::::).

(B) 1–4 EBI 2 SEQ ID NO:2 has 2 possible initiator methionine codons. Predicted transmembrane domains are indicated (single underlines). No signal peptide sequence was identified. The amino terminal extracellular segment contains a potential N-linked glycosylation site (CHO######).

Figure 2:
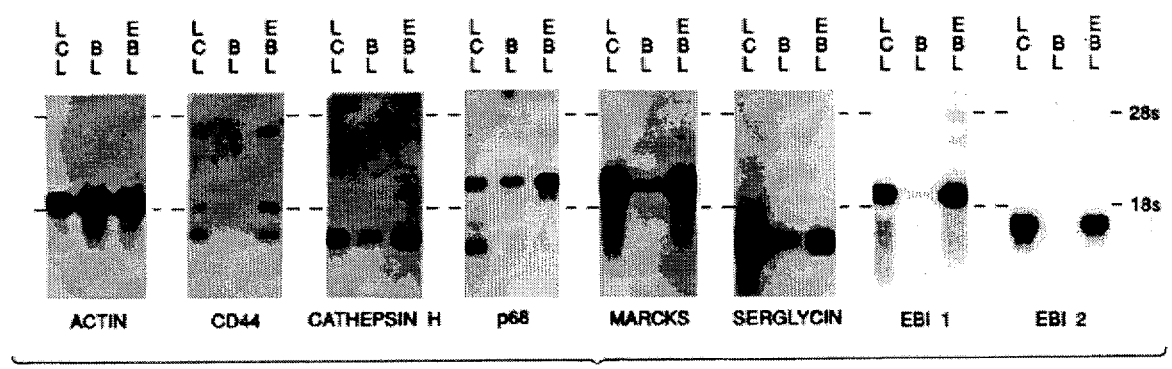

FIG. 2. RNA blot hybridization analysis of EBV induced cellular gene expression. Polyadenylylated (4 to 12 μg per lane) was size fractionated on formaldehyde agarose gels, transferred to charged nylon membranes, and hybridized with the probes indicated at the bottom of each autoradiograph panel. RNA samples used are indicated at the top of each lane (LCL:EBV immortalized primary B lymphoblastoid cell line, IB4; BL:EBV negative Burkitt lymphoma cell line, BL41; EBL:EBV infected Burkitt lymphoma cell line, BL41/B95-8, derived by in vitro infection of BL41 line). Dashes indicate positions of ribosomal RNA bands (18s, 28s). The band detected at 1.5 kb in the LCL lane by the P68 probe is due to residual signal from a prior hybridization.

Figure 3:
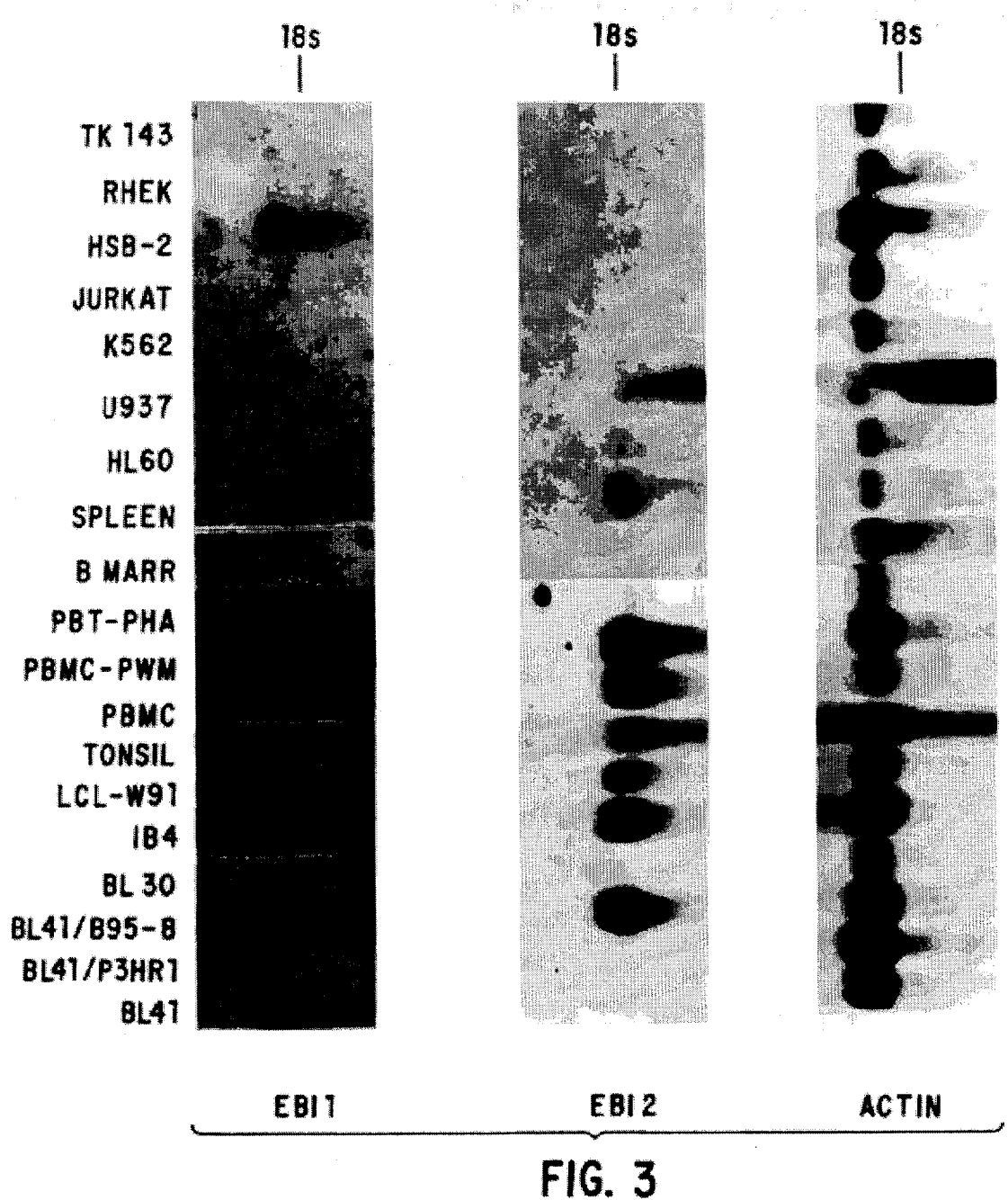

FIG. 3. Expression of EBI 1 and EBI 2 receptor genes in human lymphoid tissues and cell lines. 32P-labelled probes indicated at the left of each panel were hybridized to blots containing RNA from the cell lines indicated at the top of each lane. BL41 and BL30 are EBV-negative BL cell lines; BL41/P3HR1 is infected with a non-transforming EBV strain, p3HR1; BL4/B95-8 is infected with a transforming EBV strain; IB4 is a cell line derived by infecting primary B lymphocytes with EBV of the B95-8 strain; LCL-W91 is a recently established B lymphoblastoid cell line transformed with EBV strain W91; TONSIL is unfractionated cells from surgically excised human tonsil; PBMC is unfractionated peripheral blood mononuclear cells; PBMC PWM is PBMC stimulated 72 h with pokeweed mitogen (2.5 μg/ml); PBT PHA is T cells purified from PBMC by sheep erythrocyte rosetting, stimulated 72 h with phytohemagglutinin (1 μg/ml); B MARR is post-mortem bone marrow; SPLEEN is unfractionated cells from surgically excised spleen; HL60 is a promyelocytic leukemia cell line; U937 is a monocytic leukemia cell line; K562 is a chronic myelogenous leukemia cell line; JURKAT is a T cell leukemia cell line; HSB-2 is a T cell acute lymphoblastic leukemia cell line; RHEK-1 is an adenovirus/SV40 transformed human keratinocyte; TK143 is a osteosarcoma cell line. Each panel is a composite prepared from autoradiographs of two separate blots for each probe.

Figure 4:
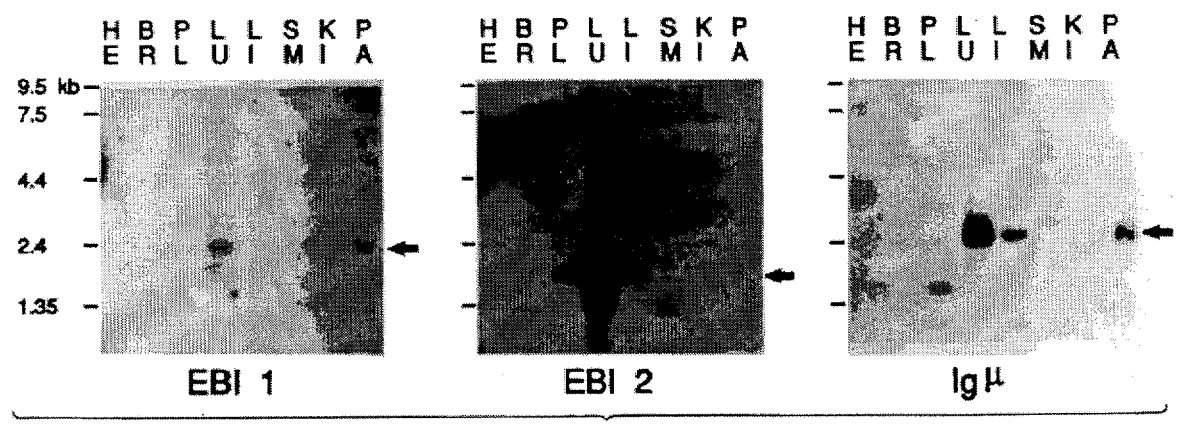

FIG. 4. EBI 1 and EBI 2 gene expression in human tissues. EBI 1, EBI 2 and immunoglobulin mu chain (IgU) probes were hybridized to RNA samples from the following human tissues: heart (HE), brain (BR), placenta (PL), lung (LU), liver (LI), kidney (KI), skeletal muscle (SM) and pancreas (PA). Numbers at the left indicate positions and sizes (in kb) of RNA markers. Specific RNA bands are indicated by arrows to the right of each panel. The EBI 1 probe detects faint 2.4 kb bands in lung and pancreas PNA. The EBI 2 probe detects an abundant 1.9 kb RNA in lung, and a faint 1.9 kb band in pancreas. The 2.7 kb Igμ RNA is detected in lung, liver and pancreas preparations. The 1.5 kb band in placental RNA hybridized with IgU probe is residual signal from a previous hybridization.

FIG. 5A–C Complete nucleotide and deduced amino acid sequences of EBI 3 cDNA. The 1161 nucleotide EBI 3 cDNA contains a 687 nucleotide open reading frame encoding a 26 kD polypeptide. A hydrophobic amino terminal segment (single underline) comprises a signal peptide for membrane translocation. No other hydrophobic segments that could potentially form a transmembrane domain are evident. Two potential asparagine-linked glycosylation sites are indicated (CHO###). The nucleotide sequence of the 3' untranslated region bears significant homology with the human Alu repeat element (light underline).

Figure 6:
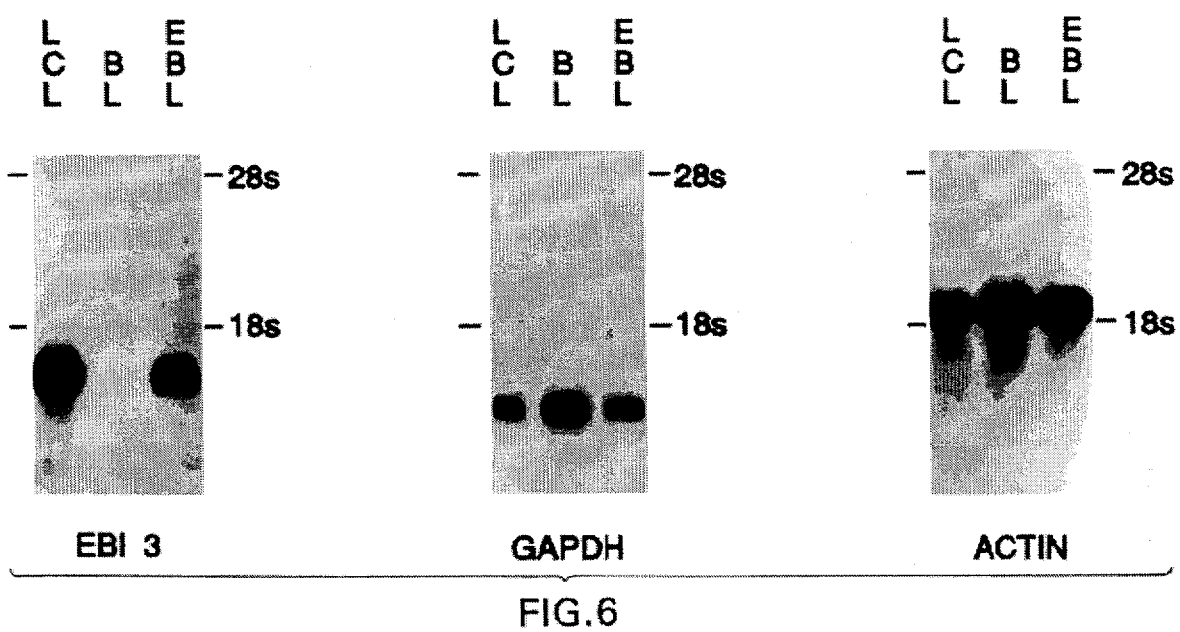

FIG. 6. RNA blot hybridization analysis of EBI 3 gene expression. Polyadenylated RNA (4 to 12 μg/lane) was size fractionated on formaldehyde agarose gel, transferred to an activated nylon membrane and hybridized with a 32P-labeled EBI 3 cDNA, actin and glyceraldehyde dehydrogenase (GAPDH) probes. RNA samples used in each lane are indicated at the top. (LCL is the EBV-immortalized primary B lymphoblastoid cell line, IB4; BL is the EBV-negative Burkitt lymphoma cell line, BL41; EBL is the EBV-infected Burkitt lymphoma cell line, BL41/B95-8, derived by in vitro infection of BL41 line.) An abundant 1.5 kb RNA is recognized by the EBI 3 probe in both EBV-infected cell line RNA samples (LCL, EBL), but is undetectable in the EBV-negative cell sample (BL). Control hybridization with actin and GAPDH probes indicate that the BL lane contains as much or more RNA than the EBV-infected cell lanes. Dashes indicate positions of ribosomal RNA bands (18s, 28s).

FIG. 7. Expression of EBI 3 gene RNA in human tissues and cell lines.

EBI 3 or actin probes were hybridized to blots containing RNA from the cell lines or lymphoid tissues indicated at the top of each lane. (A) Louckes, BL30 and BL41 are EBV(−) Burkitt lymphoma cell lines; BL41/B95-8 is infected with the transforming, B95-8 strain of EBV; IB4, W91, and SLA are EBV-transformed lymphoblastoid cell lines; P3HR1 is an EBV(+) BL cell line infected with the non-transforming P3HR1 EBV; Jurkat and MOLT4 are human T cell lines; MARROW is post-mortem costal bond marrow; SPLEEN is unfractionated cells from surgically excised normal human spleen; TONSIL represents unfractionated cells from surgically excised human tonsil; PBMC is unfractionated peripheral blood mononuclear cells; PBMC-PWM is PBMC stimulated for 72 h with pokeweed mitogen (2.5 ug/ml); HL60 is a promyelocytic leukemia cell line; U937 is a histiocytic lymphoma cell line with monocyte features; K562 is a chronic myelogenous leukemia cell line; Jurkat is a T cell leukemia; TK143 is an osteosarcoma line; RHEK-1 is a human keratinocyte line; Hela is a cervical epithelial cell line. Each autoradiographic panel was generated from two separate blots.

(B) EBI 3 was hybridized to a commercially prepared blot (Multiple Tissue Northern, Clontech, Calif.) containing polyadenylated RNA (2 μg/lane) from each of the following human tissues: heart (HE), brain BR), placenta (PL), lung (LU), liver (LI), kidney (KI), skeletal muscle (SM) and pancreas (PA). The EBI 3 probe specifically detects an abundant 1.5 kb RNA in the placental RNA preparation (position indicated by arrow). A faint band of similar size if also observed in liver RNA. Numbers at the left indicate positions and sizes (in kb) of RNA markers.

DEFINITIONS

In the description that follows, a number of terms used in recombinant DNA (rDNA) technology are extensively utilized. In order to provide a clear and consistent understanding of the specification and claims, including the scope to be given such terms, the following definitions are provided.

DNA segment. A DNA segment, as is generally understood and used herein, refers to a molecule comprising a linear stretch of nucleotides wherein the nucleotides are present in a sequence that may encode, through the genetic code, a molecule comprising a linear sequence of amino acid residues that is referred to as a protein, a protein fragment or a polypeptide.

Gene. A DNA sequence related to a single polypeptide chain or protein, and as used herein includes the 5' and 3' untranslated ends. The polypeptide can be encoded by a full-length sequence or any portion of the coding sequence, so long as the functional activity of the protein is retained.

A "complementary DNA" or "cDNA" gene includes recombinant genes synthesized by reverse transcription of messenger RNA ("mRNA").

Structural gene. A DNA sequence that is transcribed into mRNA that is then translated into a sequence of amino acids characteristic of a specific polypeptide.

Restriction Endonuclease. A restriction endonuclease (also restriction enzyme) is an enzyme that has the capacity to recognize a specific base sequence (usually 4, 5, or 6 base pairs in length) in a DNA molecule, and to cleave the DNA molecule at every place where this sequence appears. For example, EcoRI recognizes the base sequence GAATTC/CTTAAG.

Restriction Fragment. The DNA molecules produced by digestion with a restriction endonuclease are referred to as restriction fragments. Any given genome may be digested by a particular restriction endonuclease into a discrete set of restriction fragments.

Agarose Gel Electrophoresis. To detect a polymorphism in the length of restriction fragments, an analytical method for fractionating double-stranded DNA molecules on the basis of size is required. The most commonly used technique (though not the only one) for achieving such a fractionation is agarose gel electrophoresis. The principle of this method is that DNA molecules migrate through the gel as though it were a sieve that retards the movement of the largest molecules to the greatest extent and the movement of the smallest molecules to the least extent. Note that the smaller the DNA fragment, the greater the mobility under electrophoresis in the agarose gel.

The DNA fragments fractionated by agarose gel electrophoresis can be visualized directly by a staining procedure if the number of fragments included in the pattern is small. The DNA fragments of genomes can be visualized successfully. However, most genomes, including the human genome, contain far too many DNA sequences to produce a simple pattern of restriction fragments. For example, the human genome is digested into approximately 1,000,000 different DNA fragments by EcoRI. In order to visualize a small subset of these fragments, a methodology referred to as the Southern hybridization procedure can be applied.

Southern Transfer Procedure. The purpose of the Southern transfer procedure (also referred to as blotting) is to physically transfer DNA fractionated by agarose gel electrophoresis onto a nitrocellulose filter paper or another appropriate surface or method, while retaining the relative positions of DNA fragments resulting from the fractionation procedure. The methodology used to accomplish the transfer from agarose gel to nitrocellulose involves drawing the DNA from the gel into the nitrocellulose paper by capillary action.

Nucleic Acid Hybridization. Nucleic acid hybridization depends on the principle that two single-stranded nucleic acid molecules that have complementary base sequences will reform the thermodynamically favored double-stranded structure if they are mixed under the proper conditions. The double-stranded structure will be formed between two complementary single-stranded nucleic acids even if one is immobilized on a nitrocellulose filter. In the Southern hybridization procedure, the latter situation occurs. As noted previously, the DNA of the individual to be tested is digested with a restriction endonuclease, fractionated by agarose gel electrophoresis, converted to the single-stranded form, and transferred to nitrocellulose paper, making it available for reannealing to the hybridization probe.

Hybridization Probe. To visualize a particular DNA sequence in the Southern hybridization procedure, a labeled DNA molecule or hybridization probe is reacted to the fractionated DNA bound to the nitrocellulose filter. The areas on the filter that carry DNA sequences complementary to the labeled DNA probe become labeled themselves as a consequence of the reannealing reaction. The areas of the filter that exhibit such labeling are visualized. The hybridization probe is generally produced by molecular cloning of a specific DNA sequence.

Oligonucleotide or Oligomer. A molecule comprised of two or more deoxyribonucleotides or ribonucleotides, preferably more than three. Its exact size will depend on many factors, which in turn depend on the ultimate function or use of the oligonucleotide. An oligonucleotide may be derived synthetically or by cloning.

Sequence Amplification. A method for generating large amounts of a target sequence. In general, one or more amplification primers are annealed to a nucleic acid sequence. Using appropriate enzymes, sequences found adjacent to, or in between the primers are amplified.

Amplification Primer. An oligonucleotide which is capable of annealing adjacent to a target sequence and serving as an initiation point for DNA synthesis when placed under conditions in which synthesis of a primer extension product which is complementary to a nucleic acid strand is initiated.

Vector. A plasmid or phage DNA or other DNA sequence into which DNA may be inserted to be cloned. The vector may replicate autonomously in a host cell, and may be further characterized by one or a small number of endonuclease recognition sites at which such DNA sequences may be cut in a determinable fashion and into which DNA may be inserted. The vector may further contain a marker suitable for use in the identification of cells transformed with the vector. Markers, for example, are tetracycline resistance or ampicillin resistance. The words "cloning vehicle" are sometimes used for "vector."

Expression. Expression is the process by which a structural gene produces a polypeptide. It involves transcription of the gene into mRNA, and the translation of such mRNA into polypeptide(s).

Expression vector. A vector or vehicle similar to a cloning vector but which is capable of expressing a gene which has been cloned into it, after transformation into a host. The cloned gene is usually placed under the control of (i.e., operably linked to) certain control sequences such as promoter sequences.

Expression control sequences will vary depending on whether the vector is designed to express the operably linked gene in a prokaryotic or eukaryotic host and may additionally contain transcriptional elements such as enhancer elements, termination sequences, tissue-specificity elements, and/or translational initiation and termination sites.

Functional Derivative. A "functional derivative" of a sequence, either protein or nucleic acid, is a molecule that possesses a biological activity (either functional or structural) that is substantially similar or antagonistic to a biological activity of the protein or nucleic acid sequence. A functional derivative of a protein may or may not contain post-translational modifications such as covalently linked carbohydrate, depending on the necessity of such modifications for the performance of a specific function. The term "functional derivative" is intended to include the "fragments," "segments," "variants," "analogs," or "chemical derivatives" of a molecule.

As used herein, a molecule is said to be a "chemical derivative" of another molecule when it contains additional chemical moieties not normally a part of the molecule. Such moieties may improve the molecule's solubility, absorption, biological half life, and the like. The moieties may alternatively decrease the toxicity of the molecule, eliminate or attenuate any undesirable side effect of the molecule, and the like. Moieties capable of mediating such effects are disclosed in Remington's Pharmaceutical Sciences (1980). Procedures for coupling such moieties to a molecule are well known in the art.

Fragment. A "fragment" of a molecule such as a protein or nucleic acid is meant to refer to any portion of the amino acid or nucleotide genetic sequence.

Variant. A "variant" of a protein or nucleic acid is meant to refer to a molecule substantially similar in structure and biological activity to either a the protein or nucleic acid, or to a fragment thereof. Thus, provided that two molecules possess a common activity and may substitute for each other, they are considered variants as that term is used herein even if the composition or secondary, tertiary, or quaternary structure of one of the molecules is not identical to that found in the other, or if the amino acid or nucleotide sequence is not identical.

Analog. An "analog" of a protein or genetic sequence is meant to refer to a protein or genetic sequence substantially similar in function to a protein or genetic sequence described herein.

Allele. An "allele" is an alternative form of a gene occupying a given locus on the chromosome.

Mutation. A "mutation" is any detectable change in the genetic material which may be transmitted to daughter cells and possibly even to succeeding generations giving rise to mutant cells or mutant individuals. If the descendants of a mutant cell give rise only to somatic cells in multicellular organisms, a mutant spot or area of cells arises. Mutations in the germ line of sexually reproducing organisms may be transmitted by the gametes to the next generation resulting in an individual with the new mutant condition in both its somatic and germ cells. A mutation may be any (or a combination of) detectable, unnatural change affecting the chemical or physical constitution, mutability, replication, phenotypic function, or recombination of one or more deoxyribonucleotides; nucleotides may be added, deleted, substituted for, inverted, or transposed to new positions with and without inversion. Mutations may occur spontaneously and can be induced experimentally by application of mutagens. A mutant variation of a DNA segment results from a mutation. A mutant polypeptide may result from a mutant DNA segment.

Species. A "species" is a group of actually or potentially interbreeding natural populations. A species variation within a DNA segment or protein is a change in the nucleic acid or amino acid sequence that occurs among species and may be determined by DNA sequencing of the segment in question.

Substantially Pure. A "substantially pure" protein or nucleic acid is a protein or nucleic acid preparation that is generally lacking in other cellular components.

DETAILED DESCRIPTION OF THE PREFERRED EMBODIMENTS

The present invention relates to novel DNA sequences, EBI 1, EBI 2, and EBI 3, which have been identified as Epstein Barr virus induced genes.

A. DNA segments coding for EBI 1, EBI 2, and EBI 3 polypeptides, and fragments thereof In one embodiment, the present invention relates to a DNA segment coding for a polypeptide having an amino acid sequence corresponding to a polypeptide selected from the group consisting of EBI 1, EBI 2, and EBI 3 polypeptides, or at least 7 contiguous amino acids thereof (preferably, at least 10, 15, 20, or 30 contiguous amino acids thereof). In one preferred embodiment, the DNA segment comprises the sequences set forth in SEQ ID NO:1, SEQ ID NO:3, or SEQ ID NO:5; allelic, mutant or species variation thereof, or at least 20 contiguous nucleotides thereof (preferably at least 25, 30, 40, or 50 contiguous nucleotides thereof). In another preferred embodiment, the DNA segment encodes an amino acid sequence selected from the group consisting of sequences set forth in SEQ ID NO:2, SEQ ID NO:4, and SEQ ID NO:6, or mutant or species variation thereof, or at least 7 contiguous amino acids thereof (preferably, at least 10, 15, 20, or 30 contiguous amino acids thereof).

Also included within the scope of this invention are the functional equivalents of the herein-described DNA or nucleotide sequences. The degeneracy of the genetic code permits substitution of certain codons by other codons which specify the same amino acid and hence would give rise to the same protein. The DNA or nucleotide sequence can vary substantially since, with the exception of methionine and tryptophan, the known amino acids can be coded for by more than one codon. Thus, portions or all of the EBI 1, EBI 2, or EBI 3 gene could be synthesized to give a DNA sequence significantly different from that shown in SEQ ID NO: 1, SEQ ID NO:3, or SEQ ID NO:5. The encoded amino acid sequence thereof would, however, be preserved.

In addition, the DNA or nucleotide sequence may comprise a nucleotide sequence which results from the addition, deletion or substitution of at least one nucleotide to the 5'-end and/or the 3'-end of the DNA formula shown in SEQ ID NO:1, SEQ ID NO:3, or SEQ ID NO:5 or a derivative thereof. Any nucleotide or polynucleotide may be used in this regard, provided that its addition, deletion or substitution does not alter the amino acid sequence of SEQ ID NO:2, SEQ ID NO:4, or SEQ ID NO:6 which is encoded by the nucleotide sequence. For example, the present invention is intended to include any nucleotide sequence resulting from the addition of ATG as an initiation codon at the 5'-end of the inventive nucleotide sequence or its derivative, or from the addition of TTA, TAG or TGA as a termination codon at the 3'-end of the inventive nucleotide sequence or its derivative. Moreover, the DNA fragment of the present invention may, as necessary, have restriction endonuclease recognition sites added to its 5'-end and/or 3'-end.

Such functional alterations of a given DNA or nucleotide sequence afford an opportunity to promote secretion and/or processing of heterologous proteins encoded by foreign DNA sequences fused thereto. All variations of the nucleotide sequence of the EBI 1, EBI 2, and EBI 3 genes and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified DNA molecule. As recognized in the art, the two polypeptides are functionally equivalent, as are the two DNA molecules which give rise to their production, even though the differences between the DNA molecules are not related to degeneracy of the genetic code.

A.1. Isolation of DNA.

In one aspect of the present invention, DNA segments coding for polypeptides having amino acid sequences corresponding to EBI 1, EBI 2, and EBI 3 are provided. In particular, the DNA segment may be isolated from a biological sample containing RNA or DNA.

The DNA segment may be isolated from a biological sample containing RNA using the techniques of cDNA cloning and subtractive hybridization as previously described (Birkenbach et al., *J. of Virology* 63:9:4079–4084). The DNA segment may also be isolated from a cDNA library using a homologous probe.

The DNA segment may be isolated from a biological sample containing genomic DNA or from a genomic library using techniques well known in the art. Suitable biological samples include, but are not limited to, blood, semen and tissue. The method of obtaining the biological sample will vary depending upon the nature of the sample.

One skilled in the art will realize that the human genome may be subject to slight allelic variations between individuals. Therefore, the isolated DNA segment is also intended to include allelic variations, so long as the sequence is a functional derivative of the EBI 1, EBI 2, or EBI 3 gene.

One skilled in the art will realize that organisms other than humans may also contain EBI 1, EBI 2, or EBI 3 genes (for example, eukaryotes; more specifically, mammals, birds, fish, and plants; more specifically, gorillas, rhesus monkeys, and chimpanzees). The invention is intended to include, but not be limited to, EBI 1, EBI 2, and EBI 3 DNA segments isolated from the above-described organisms.

A.2. Synthesis of DNA.

In the alternative, the DNA segment of the present invention may be chemically synthesized. For example, a DNA fragment with the nucleotide sequence which codes for the expression product of an EBI 1, EBI 2, or EBI 3 gene may be designed and, if necessary, divided into appropriate smaller fragments. Then an oligomer which corresponds to the DNA fragment, or to each of the divided fragments, may be synthesized. Such synthetic oligonucleotides may be prepared, for example, by the triester method of Matteucci et al., *J. Am. Chem. Soc.* 103:3185–3191 (1981) or by using an automated DNA synthesizer.

An oligonucleotide may be derived synthetically or by cloning. If necessary, the 5'-ends of the oligomers may be phosphorylated using T4 polynucleotide kinase. Kinasing of single strands prior to annealing or for labeling may be achieved using an excess of the enzyme. If kinasing is for the labeling of probe, the ATP may contain high specific activity radioisotopes. Then, the DNA oligomer may be subjected to annealing and ligation with T4 ligase or the like.

B. A substantially pure EBI 1, EBI 2, and EBI 3 polypeptides

In another embodiment, the present invention relates to a substantially pure polypeptide having an amino acid sequence corresponding to a polypeptide selected from the group consisting of EBI 1, EBI 2, and EBI 3 polypeptides, or at least 7 contiguous amino acids thereof (preferably, at least 10, 15, 20, or 30 contiguous amino acids thereof). In a preferred embodiment, the polypeptide has an amino acid sequence selected from the group consisting of sequences set forth in SEQ ID NO:2, SEQ ID NO:4, and SEQ ID NO:6, or mutant or species variation thereof, or at least 7 contiguous amino acids thereof (preferably, at least 10, 15, 20, or 30 contiguous amino acids thereof).

A variety of methodologies known in the art can be utilized to obtain the peptide of the present invention. In one embodiment, the peptide is purified from tissues or cells which naturally produce the peptide. The samples of the present invention include cells, protein extracts or membrane extracts of cells, or biological fluids. The sample will vary based on the assay format, the detection method and the nature of the tissues, cells or extracts used as the sample.

Any eukaryotic organism can be used as a source for the peptide of the invention, as long as the source organism naturally contains such a peptide. As used herein, "source organism" refers to the original organism from which the amino acid sequence of the subunit is derived, regardless of the organism the subunit is expressed in and ultimately isolated from.

One skilled in the art can readily follow known methods for isolating proteins in order to obtain the peptide free of natural contaminants. These include, but are not limited to: immunochromotography, size-exclusion chromatography, HPLC, ion-exchange chromatography, and immuno-affinity chromatography.

C. A nucleic acid probe for the detection of Epstein Barr virus

In another embodiment, the present invention relates to a nucleic acid probe for the detection of the presence of Epstein Barr Virus in a sample comprising the above-described DNA segments or at least 20 contiguous nucleotides thereof (preferably at least 25, 30, 40, or 50 thereof).

In another preferred embodiment, the DNA segment has a nucleic acid sequence selected from the group consisting of sequences set forth in SEQ ID NO: 1, SEQ ID NO:3, and SEQ ID NO:5, or at least 20 contiguous nucleotides thereof (preferably at least 25, 30, 40, or 50 thereof). In another preferred embodiment, the nucleic acid probe encodes an amino acid sequence selected from the group consisting of sequences set forth in SEQ ID NO:2, SEQ ID NO:4, and SEQ ID NO:6, or at least 7 contiguous amino acids thereof.

The nucleic acid probe may be used to probe an appropriate chromosomal or cDNA library by usual hybridization methods to obtain another DNA segment of the present invention. A chromosomal DNA or cDNA library may be prepared from appropriate cells according to recognized methods in the art (cf. *Molecular Cloning: A Laboratory Manual*, second edition, edited by Sambrook, Fritsch, & Maniatis, Cold Spring Harbor Laboratory, 1989).

In the alternative, chemical synthesis is carried out in order to obtain nucleic acid probes having nucleotide sequences which correspond to N-terminal and C-terminal portions of the amino acid sequence of the polypeptide of interest. Thus, the synthesized nucleic acid probes may be used as primers in a polymerase chain reaction (PCR) carried out in accordance with recognized PCR techniques, essentially according to PCR *Protocols, A Guide to Methods and Applications*, edited by Michael et al., Academic Press, 1990, utilizing the appropriate chromosomal or cDNA library to obtain the fragment of the present invention.

One skilled in the art can readily design such probes based on the sequence disclosed herein using methods of computer alignment and sequence analysis known in the art (cf. *Molecular Cloning: A Laboratory Manual*, second edition, edited by Sambrook, Fritsch, & Maniatis, Cold Spring Harbor Laboratory, 1989).

The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

The nucleic acid probes of the present invention include RNA, as well as DNA probes, such probes being generated using techniques known in the art.

In one embodiment of the above described method, a nucleic acid probe is immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

D. A method of detecting the presence of Epstein Barr virus in a sample

In another embodiment, the present invention relates to a method of detecting the presence of Epstein Barr virus in a sample comprising a) contacting said sample with the above-described nucleic acid probe, under conditions such that hybridization occurs, and b) detecting the presence of said probe bound to said DNA segment. One skilled in the art would select the nucleic acid probe according to techniques known in the art as described above. Samples to be tested include but should not be limited to RNA samples of human tissue. The presence of EBI 1, EBI 2, or EBI 3 may represent that the cells had been infected with the Epstein Barr virus. Increases in the amount of EBI 1, EBI 2, or EBI 3 RNA in a sample may also indicate the presence of or infection with the Epstein Barr virus.

E. A kit for detecting the presence of Epstein Barr virus in a sample

In another embodiment, the present invention relates to a kit for detecting the presence of Epstein Barr virus in a sample comprising at least one container means having disposed therein the above-described nucleic acid probe. In a preferred embodiment, the kit further comprises other containers comprising one or more of the following: wash reagents and reagents capable of detecting the presence of bound nucleic acid probe. Examples of detection reagents include, but are not limited to radiolabelled probes, enzymatic labeled probes (horse radish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like.

One skilled in the art will readily recognize that the nucleic acid probes described in the present invention can readily be incorporated into one of the established kit formats which are well known in the art.

F. DNA constructs comprising the EBI 1, EBI 2, or EBI 3 DNA segments and cells containing these constructs In another embodiment, the present invention relates to a recombinant DNA molecule comprising, 5' to 3', a promoter effective to initiate transcription in a host cell and the above-described DNA segments.

In another embodiment, the present invention relates to a recombinant DNA molecule comprising a vector and an above-described DNA segment.

In another embodiment, the present invention relates to a DNA molecule comprising a transcriptional region functional in a cell, a sequence complimentary to an RNA sequence encoding an amino acid sequence corresponding to the above-described polypeptide, and a transcriptional termination region functional in said cell.

Preferably, the above-described molecules are isolated and/or purified DNA molecules.

In another embodiment, the present invention relates to a cell that contains an above-described DNA molecule.

In another embodiment, the peptide is purified from cells which have been altered to express the peptide.

As used herein, a cell is said to be "altered to express a desired peptide" when the cell, through genetic manipulation, is made to produce a protein which it normally does not produce or which the cell normally produces at low levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding an EBI 1, EBI 2, or EBI 3 gene may be obtained by the above-described methods. This region may be retained for its transcriptional termination regulatory sequences, such as termination and polyadenylation. Thus, by retaining the 3'-region naturally contiguous to the DNA sequence encoding an EBI 1, EBI 2, or EBI 3 gene, the transcriptional termination signals may be provided. Where the transcriptional termination signals are not satisfactorily functional in the expression host cell, then a 3' region functional in the host cell may be substituted.

Two DNA sequences (such as a promoter region sequence and an EBI 1, EBI 2, or EBI 3 sequence) are said to be operably linked if the nature of the linkage between the two DNA sequences does not (1) result in the introduction of a frame-shift mutation, (2) interfere with the ability of the promoter region sequence to direct the transcription of an EBI 1, EBI 2, EBI 3 gene sequence, or (3) interfere with the ability of the an EBI 1, EBI 2, or EBI 3 gene sequence to be transcribed by the promoter region sequence. Thus, a promoter region would be operably linked to a DNA sequence if the promoter were capable of effecting transcription of that DNA sequence.

Thus, to express an EBI 1, EBI 2, or EBI 3 gene, transcriptional and translational signals recognized by an appropriate host are necessary.

The present invention encompasses the expression of the EBI 1, EBI 2, or EBI 3 gene (or a functional derivative thereof) in either prokaryotic or eukaryotic cells. Prokaryotic hosts are, generally, the most efficient and convenient for the production of recombinant proteins.

Prokaryotes most frequently are represented by various strains of E. coli. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC18, pUC19 and the like; suitable phage or bacteriophage vectors may include λgt10, λgt11 and the like; and suitable virus vectors may include pMAM-neo, pKRC and the like. Preferably, the selected vector of the present invention has the capacity to replicate in the selected host cell.

Recognized prokaryotic hosts include bacteria such as E. coli, Bacillus, Streptomyces, Pseudomonas, Salmonella, Serratia, and the like. However, under such conditions, the peptide will not be glycosylated. The prokaryotic host must be compatible with the replicon and control sequences in the expression plasmid.

To express EBI 1, 2, or 3 (or a functional derivative thereof) in a prokaryotic cell, it is necessary to operably link the EBI 1, EBI 2, or EBI 3 sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ ($P_L$ and $P_R$), the trp, recA, lacZ, lacI, and gal promoters of E. coli, the α-amylase (Ulmanen et al., J. Bacteriol. 162:176–182 (1985)) and the ζ-28-specific promoters of B. subtilis (Gilman et al., Gene sequence 32:11–20 (1984)), the promoters of the bacteriophages of Bacillus (Gryczan, In: The Molecular Biology of the Bacilli, Academic Press, Inc., NY (1982)), and Streptomyces promoters (Ward et al., Mol. Gen. Genet. 203:468–478 (1986)).

Prokaryotic promoters are reviewed by Glick (J. Ind. Microbiol. 1:277–282 (1987)); Cenatiempo (Biochimie 68:505–516 (1986)); and Gottesman (Ann. Rev. Genet. 18:415–442 (1984)).

Proper expression in a prokaryotic cell also requires the presence of a ribosome binding site upstream of the gene sequence-encoding sequence. Such ribosome binding sites are disclosed, for example, by Gold et al. (Ann. Rev. Microbiol. 35:365–404 (1981)).

The selection of control sequences, expression vectors, transformation methods, and the like, are dependent on the type of host cell used to express the gene. As used herein, "cell", "cell line", and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the EBI 1, 2, or 3 peptide of interest. Suitable hosts may often include eukaryotic cells.

Preferred eukaryotic hosts include, for example, yeast, fungi, insect cells, mammalian cells either in vivo, or in tissue culture. Mammalian cells which may be useful as hosts include HeLa cells, cells of fibroblast origin such as VERO or CHO-K1, or cells of lymphoid origin, such as the hybridoma SP2/O-AG14 or the myeloma P3x63Sg8, and their derivatives. Preferred mammalian host cells include SP2/0 and J558L, as well as neuroblastoma cell lines such as IMR 332 that may provide better capacities for correct post-translational processing.

In addition, plant cells are also available as hosts, and control sequences compatible with plant cells are available, such as the nopaline synthase promoter and polyadenylation signal sequences.

Another preferred host is an insect cell, for example the Drosophila larvae. Using insect cells as hosts, the Drosophila alcohol dehydrogenase promoter can be used Rubin, Science 240:1453–1459 (1988). Alternatively, baculovirus vectors can be engineered to express large amounts of EBI 1, EBI 2, or EBI 3 in insects cells (Jasny, Science 238:1653 (1987); Miller et al., In: Genetic Engineering (1986), Setlow, J. K., et al., eds., Plenum, Vol. 8, pp. 277–297).

Any of a series of yeast gene sequence expression systems can be utilized which incorporate promoter and termination elements from the actively expressed gene sequences coding for glycolytic enzymes are produced in large quantities when yeast are grown in mediums rich in glucose. Known glycolytic gene sequences can also provide very efficient transcriptional control signals.

Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of EBI 1, EBI 2, or EBI 3.

A wide variety of transcriptional and translational regulatory sequences may be employed, depending upon the nature of the host. The transcriptional and translational regulatory signals may be derived from viral sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperaturesensitive so that by varying the temperature, expression can be repressed or initiated, or are subject to chemical (such as metabolite) regulation.

As discussed above, expression of EBI 1, EBI 2, or EBI 3 in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288 (1982)); the TK promoter of Herpes virus (McKnight, *Cell* 31:355–365 (1982)); the SV40 early promoter (Benoist et al., *Nature (London)* 290:304–310 (1981)); the yeast gal4 gene sequence promoter (Johnston et al., *Proc. Natl. Acad. Sci. (USA)* 79:6971–6975 (1982); Silver et al., *Proc. Natl. Acad. Sci. (USA)* 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes EBI 1, EBI 2, or EBI 3 (or a functional derivative thereof) does not contain any intervening codons which are capable of encoding a methionine (i.e., AUG). The presence of such codons results either in a formation of a fusion protein (if the AUG codon is in the same reading frame as the EBI 1, EBI 2, or EBI 3 coding sequence) or a frame-shift mutation (if the AUG codon is not in the same reading frame as the EBI 1, EBI 2, or EBI 3 coding sequence).

An EBI 1, EBI 2, or EBI 3 DNA segment and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the gene may occur through the transient expression of the introduced sequence. Alternatively, permanent expression may occur through the integration of the introduced DNA sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, *Molec. Cell. Biol.* 3:280 (1983).

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coli* (such as, for example, pBR322, ColE1, pSC101, pACYC 184, πVX. Such plasmids are, for example, disclosed by Sambrook (cf. *Molecular Cloning: A Laboratory Manual*, second edition, edited by Sambrook, Fritsch, & Maniatis, Cold Spring Harbor Laboratory, 1989)). Bacillus plasmids include pC194, pC221, pT127, and the like. Such plasmids are disclosed by Gryczan (In: *The Molecular Biology of the Bacilli*, Academic Press, NY (1982), pp. 307–329). Suitable Streptomyces plasmids include pIJ101 (Kendall et al., *J. Bacteriol.* 169:4177–4183 (1987)), and streptomyces bacteriophages such as φC31 (Chater et al., In: *Sixth International Symposium on Actinomycetales Biology*, Akademiai Kaido, Budapest, Hungary (1986), pp. 45–54). Pseudomonas plasmids are reviewed by John et al. (*Rev. Infect. Dis.* 8:693–704 (1986)), and Izaki (Jpn. *J. Bacteriol.* 33:729–742 (1978)).

Preferred eukaryotic plasmids include, for example, BPV, vaccinia, SV40, 2-micron circle, and the like, or their derivatives. Such plasmids are well known in the art (Botstein et al., *Miami Wntr. Symp.* 19:265–274 (1982); Broach, In: *The Molecular Biology of the Yeast Saccharomyces: Life Cycle and Inheritance*, Cold Spring Harbor Laboratory, Cold Spring Harbor, N.Y., p. 445–470 (1981); Broach, *Cell* 28:203–204 (1982); Bollon et al., *J. Clin. Hematol. Oncol.* 10:39–48 (1980); Maniatis, In: *Cell Biology: A Comprehensive Treatise*, Vol. 3, Gene Sequence Expression, Academic Press, NY, pp. 563–608 (1980)).

Once the vector or DNA sequence containing the construct(s) has been prepared for expression, the DNA construct(s) may be introduced into an appropriate host cell by any of a variety of suitable means, i.e., transformation, transfection, conjugation, protoplast fusion, electroporation, calcium phosphate-precipitation, direct microinjection, and the like. After the introduction of the vector, recipient cells are grown in a selective medium, which selects for the growth of vector-containing cells. Expression of the cloned gene sequence(s) results in the production of EBI 1, EBI 2, or EBI 3, or fragments thereof. This can take place in the transformed cells as such, or following the induction of these cells to differentiate (for example, by administration of bromodeoxyuracil to neuroblastoma cells or the like).

A variety of incubation conditions can be used to form the peptide of the present invention. The most preferred conditions are those which mimic physiological conditions.

G. An antibody having binding affinity to an EBI 1, EBI 2, and EBI 3 polypeptide, or a binding fragment thereof and a hybridoma containing the antibody In another embodiment, the present invention relates to an antibody having binding affinity to a polypeptide having an amino acid sequence selected from the group consisting of EBI 1, EBI 2, and EBI 3 polypeptides, or a binding fragment thereof. In a preferred embodiment, the polypeptide has an amino acid sequence selected from the group of sequences set forth in SEQ ID NO:2, SEQ ID NO:4, and SEQ ID NO:6, or mutant or species variation thereof, or at least 7 contiguous amino acids thereof (preferably, at least 10, 15, 20, or 30 contiguous amino acids thereof). In another preferred embodiment, the antibody is a monoclonal antibody.

In another embodiment, the present invention relates to a hybridoma which produces the above-described monoclonal antibody, or binding fragment thereof.

The EBI 1, EBI 2, or EBI 3 proteins of the present invention can be used in a variety of procedures and methods, such as for the generation of antibodies, for use in identifying pharmaceutical compositions, and for studying DNA/protein interaction.

The EBI 1, EBI 2, or EBI 3 peptide of the present invention can be used to produce antibodies or hybridomas. One skilled in the art will recognize that if an antibody is desired, such a peptide would be generated as described herein and used as an immunogen.

The antibodies of the present invention include monoclonal and polyclonal antibodies, as well fragments of these antibodies, and humanized forms. Humanized forms of the antibodies of the present invention may be generated using one of the procedures known in the art such as chimerization or CDR grafting.

The invention also provides hybridomas which are capable of producing the above-described antibodies. A hybridoma is an immortalized cell line which is capable of secreting a specific monoclonal antibody.

In general, techniques for preparing monoclonal antibodies and hybridomas are well known in the art (Campbell, "*Monoclonal Antibody Technology: Laboratory Techniques in Biochemistry and Molecular Biology,*" Elsevier Science Publishers, Amsterdam, The Netherlands (1984); St. Groth et al., *J. Immunol. Methods* 35:1–21 (1980)).

Any animal (mouse, rabbit, and the like) which is known to produce antibodies can be immunized with the selected polypeptide. Methods for immunization are well known in the art. Such methods include subcutaneous or interperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109–124 (1988)).

Hybridomas secreting the desired antibodies are cloned and the class and subclass is determined using procedures known in the art (Campbell, *Monoclonal Antibody Technology: Laboratory Techniques in Biochemistry and Molecular Biology*, supra (1984)).

For polyclonal antibodies, antibody containing antisera is isolated from the immunized animal and is screened for the presence of antibodies with the desired specificity using one of the above-described procedures.

In another embodiment of the present invention, the above-described antibodies are detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Sternberger et al., *J. Histochem. Cytochem.* 18:315 (1970); Bayer et al., *Meth. Enzym.* 62:308 (1979); Engval et al., Immunol. 109:129 (1972); Goding, *J. Immunol. Meth.* 13:215 (1976)). The labeled antibodies of the present invention can be used for in vitro, in vivo, and in situ assays to identify cells or tissues which express a specific peptide.

In another embodiment of the present invention the above-described antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "*Handbook of Experimental Immunology*" 4th Ed., Blackwell Scientific Publications, Oxford, England, Chapter 10 (1986); Jacoby et al., *Meth. Enzym.* 34 Academic Press, N.Y. (1974)). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", *In Synthetic Peptides, A User's Guide*, W. H. Freeman, NY, pp. 289–307 (1992), and Kaspczak et al., *Biochemistry* 28:9230–8 (1989).

Anti-peptide peptides can be generated in one of two fashions. First, the anti-peptide peptides can be generated by replacing the basic amino acid residues found in the EBI 1, EBI 2, or EBI 3 peptide sequence with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

H. A method of detecting an EBI 1, EBI 2, or EBI 3 polypeptide in a sample

In another embodiment, the present invention relates to a method of detecting a polypeptide selected from the group consisting of EBI 1, EBI 2, EBI 3 in a sample, comprising: a) contacting the sample with an above-described antibody, under conditions such that immunocomplexes form, and b) detecting the presence of said antibody bound to the polypeptide. In detail, the methods comprise incubating a test sample with one or more of the antibodies of the present invention and assaying whether the antibody binds to the test sample. The presence of an EBI 1, EBI 2, or EBI 3 polypeptide or fragment thereof in a sample may indicate the presence or infection of Epstein Barr virus.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, "*An Introduction to Radioimmunoassay and Related Techniques*" Elsevier Science Publishers, Amsterdam, The Netherlands (1986); Bullock et al., "*Techniques in Immunocytochemistry*," Academic Press, Orlando, Fla. Vol. 1 (1982), Vol. 2 (1983), Vol. 3 (1985); Tijssen, "*Practice and Theory of Enzyme Immunoassays: Laboratory Techniques in Biochemistry and Molecular Biology*," Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

I. A diagnostic kit comprising antibodies to EBI 1, EBI 2, and EBI 3

In another embodiment of the present invention, a kit is provided which contains all the necessary reagents to carry out the previously described methods of detection. The kit may comprise: i) a first container means containing an above-described antibody, and ii) second container means containing a conjugate comprising a binding partner of the antibody and a label. In another preferred embodiment, the kit further comprises one or more other containers comprising one or more of the following: wash reagents and reagents capable of detecting the presence of bound antibodies. Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit may be as described above for nucleic acid probe kits.

One skilled in the art will readily recognize that the antibodies described in the present invention can readily be incorporated into one of the established kit formats which are well known in the art.

J. Diagnostic Screening and Treatment

It is to be understood that although the following discussion is specifically directed to human patients, the teachings are also applicable to any animal that expresses EBI-3.

The diagnostic and screening methods of the invention are especially useful for a patient suspected of being at risk for developing a disease associated with an altered expression level of EBI-3 based on family history, or a patient in which it is desired to diagnose an EBI-3-related disease.

More specifically, EBI-3 can be used as a diagnostic marker of prognostic utility in neoplastic disorders. Expression of EBI-3 in a particular malignant tumor could indicate a mechanism for evasion of immune surveillance. Such tumors could respond to an immunotheropeutic regimen based upon exogenous IL-12 administration in combination with agents which inhibit EBI-3 activity, such as anti-EBI-3 monoclonal antibodies. Preferably, the method is used in trophoblastic neoplasms.

EBI-3 can also be used a prognostic marker in infectious diseases. A number of experimental models have demonstrated that IL-12-mediated induction of T helper 1 type responses is necessary for survival of hosts infected with various pathogenic organisms. A high level of EBI-3 expression could be expected in EBV-induced lymphomas arising in immunosuppressed patients. These patients may benefit from anti-EBI-3 therapies. Moreover, IL-12 responses appear to be particularly deficient in HIV infected patients with the Acquired Immuno-Deficiency Syndrome. These patients may show clinical improvement if treated with both exogenous IL-12 and anti-EBI-3 agents.

According to the invention, presymptomatic screening of an individual in need of such screening is now possible using DNA encoding the EBI-3 protein of the invention. The screening method of the invention allows a presymptomatic diagnosis, including prenatal diagnosis, of the presence of a missing or aberrant EBI-3 gene in individuals, and thus an opinion concerning the likelihood that such individual would develop or has developed an EBI-3-associated disease. This is especially valuable for the identification of carriers of altered or missing EBI-3 genes, for example, from individuals with a family history of an EBI-3-associated disease. Early diagnosis is also desired to maximize appropriate timely intervention.

In one preferred embodiment of the method of screening, a tissue sample would be taken from such individual, and screened for (1) the presence of the "normal" human EBI-3 gene; (2) the presence of EBI-3 mRNA and/or (3) the presence of EBI-3 protein. The normal human gene can be characterized based upon, for example, detection of restriction digestion patterns in "normal" versus the patient's DNA, including RFLP analysis, using DNA probes prepared against the EBI-3 sequence (or a functional fragment thereof) taught in the invention. Similarly, EBI-3 mRNA can be characterized and compared to normal EBI-3 mRNA (a) levels and/or (b) size as found in a human population not at risk of developing EBI-3-associated disease using similar probes. Lastly, EBI-3 protein can be (a) detected and/or (b) quantitated using a biological assay for EBI-3 activity or using an immunological assay and EBI-3 antibodies. When assaying EBI-3 protein, the immunological assay is preferred for its speed. An (1) aberrant EBI-3 DNA size pattern, and/or (2) aberrant EBI-3 mRNA sizes or levels and/or (3) aberrant EBI-3 protein levels would indicate that the patient is at risk for developing an EBI-3-associated disease.

The screening and diagnostic methods of the invention do not require that the entire EBI-3 DNA coding sequence be used for the probe. Rather, it is only necessary to use a fragment or length of nucleic acid that is sufficient to detect the presence of the EBI-3 gene in a DNA preparation from a normal or affected individual, the absence of such gene, or an altered physical property of such gene (such as a change in electrophoretic migration pattern).

Prenatal diagnosis can be performed when desired, using any known method to obtain fetal cells, including amniocentesis, chronic villus sampling (CVS), and fetoscopy. Prenatal chromosome analysis can be used to determine if the portion of the chromosome possessing the normal EBI-3 gene is present in a heterozygous state.

EBI-3 can be used as a natural immunosuppressive agent to reduce cytotoxic T cell-mediated responses. These agents could be used locally to prevent graft rejection, systemically to inhibit graft-versus-host disease, or systemically and locally to treat autoimmune disorders such as arthritis, etc.

EBI-3 can also be used as an immunosuppressive agent or growth factor receptor in the placenta to support, maintain or protect continued fetal development in utero during high risk pregnancy. EBI-3 can act in trophoblasts to inhibit immune responses through competition with IL-12, and can also function as a membrane associated receptor for a necessary cytokine. EBI-3 deficiency could result in spontaneous abortion or fetal morbidity through release of maternal immune responses from normal constraints, or reduced levels of a receptor component necessary for placental development. Replacement with exogenous EBI-3 could allow survival to term of some pregnancies which would otherwise abort.

In the method of treating an EBI-3-associated disease in a patient in need of such treatment, functional EBI-3 DNA can be provided to the cells of such patient in a manner and amount that permits the expression of the EBI-3 protein provided by such gene, for a time and in a quantity sufficient to treat such patient. Many vector systems are known in the art to provide such delivery to human patients in need of a gene or protein missing from the cell. For example, retrovirus systems can be used, especially modified retrovirus systems and especially herpes simplex virus systems. Such methods are provided for, in, for example, the teachings of Breakefield, X. A. et al., *The New Biologist* 3:203–218 (1991); Huang, Q. et al., *Experimental Neurology* 115:303–316 (1992), WO93/03743 and WO90/09441. Delivery of a DNA sequence encoding a functional EBI-3 protein will effectively replace the missing or mutated EBI-3 gene of the invention.

In another embodiment, the present invention relates to a method of administering EBI-3 to an animal (preferably, a mammal (specifically, a human)) in an amount sufficient to effect an altered level of EBI-3 in the animal. The administered EBI-3 could specifically effect EBI-3 associated functions. Further, since EBI-3 is expressed in placental tissue, administration of EBI-3 could be used to alter EBI-3 levels in the placenta.

One skilled in the art will appreciate that the amounts to be administered for any particular treatment protocol can readily be determined. The dosage should not be so large as to cause adverse side effects, such as unwanted cross-reactions, anaphylactic reactions, and the like. Generally, the dosage will vary with the age, condition, sex and extent of disease in the patient, counter indications, if any, and other such variables, to be adjusted by the individual physician. Dosage can vary from 0.001 mg/kg to 50 mg/kg of EBI-3, in one or more administrations daily, for one or several days. EBI-3 can be administered parenterally by injection or by gradual perfusion over time. It can be administered intravenously, intraperitoneally, intramuscularly, or subcutaneously.

Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, antimicrobials, antioxidants, chelating agents, inert gases and the like. See, generally, *Remington's Pharmaceutical Science*, 16th Ed., Mack Eds. (1980).

In another embodiment, the present invention relates to a pharmaceutical composition comprising EBI-3 in an amount sufficient to alter EBI-3 associated activity, and a pharmaceutically acceptable diluent, carrier, or excipient. Appropriate concentrations and dosage unit sizes can be readily determined by one skilled in the art as described above (See, for example, *Remington's Pharmaceutical Sciences* (16th ed., Osol, A., Ed., Mack, Easton PA (1980) and WO 91/19008).

The present invention is described in further detail in the following non-limiting examples.

EXAMPLES

The following protocols and experimental details are referenced in the examples that follow:

Cells and cell lines. BL41 and BL30 are EBV(–) Burkitt lymphoma cell lines. The BL41/B95-8 and BL41/P3HR1 cell lines were derived by infecting BL41 with the transforming EBV strain, B95-8, or with the non-transforming strain, P3HR1, respectively (Favrot, M. C., et al., *Intl. J. Cancer* 38(6):901–6 (1986)). IB4 is a latently infected B lymphoblastoid cell line established by infection of B lymphocytes with EBV (B95-8) in vitro. RHEK-1 (generous gift from Dr. Jong Rhim, National Cancer Institute, Bethesda, Mass.) is a human keratinocyte line derived by infection of primary foreskin epithelial cells with an adenovirus 12/SV40 hybrid-virus. K562 is a Philadelphia chromosome-positive human chronic myeloid leukemia cell line. U937 is a histiocytic lymphoma cell line with monocytic features. HL60 is a promyelocytic leukemia line. HSB-2 and Jurkat are human T lymphoblastic leukemia cell lines. TK143 was derived from a human osteosarcoma.

Human mononuclear cells (PBMC) were purified from peripheral blood by centrifugation on a ficoll cushion (Ficoll-Hypague, Pharmacia, Vineland, N.J.). Cells were resuspended at $1 \times 10^6$ cells/ml in RPMI medium supplemented with 20% fetal bovine serum, and were divided into parallel cultures grown 72 h with or without 2.5 µg/ml pokeweed mitogen (PWM, Sigma, St. Louis, Mo.). T cells were isolated from purified PBMCs by rosetting overnight with aminoethylisothiouronium bromide (AET) treated sheep erythrocytes at 4° C., followed by centrifugation over ficoll. Pelleted erythrocytes were lysed with ammonium chloride. The remaining T cells were resuspended in RPMI with 20% fetal bovine serum at $1 \times 10^6$ cells/ml. Phytohemagglutinin (PHA, Sigma) was added to a final concentration of 1.0 µg/ml. Cells were cultured for 72 h and harvested for extraction of total cellular RNA.

RNA preparation and analysis. Cytoplasmic RNA was isolated from exponentially growing cells by a modification of the acid phenol/guanidinium isothiocyanate extraction procedure, followed by reprecipitation in guanidinium hydrochloride/ethanol. Total cellular RNA was extracted from 0.2 to 2 g samples of human spleen and tonsil obtained from surgical specimens, and from human postmortem bone marrow. Tissues were homogenized in acid phenol/guanidinium isothiocyanate using a rotary tissue homogenizer, extracted and precipitated. After dissolution in guanidinium hydrochloride and reprecipitation with ethanol, human tissue RNA samples were resuspended in $H_2O$ and precipitated by addition of an equal volume of 8M LiCl. The polyadenylated fractions of BL41 or BL41/B95-8 RNA were purified by 2 successive cycles of chromatography on oligodeoxythymidylate cellulose. Polyadenylated IB4 RNA was purified by a single round of oligodeoxythymidylate selection. RNA samples (4 to 12 µg per lane) were size fractionated on 0.66M formaldehyde, 1% agarose gels and transferred to charged nylon membranes (GeneScreen Plus, New England Nuclear, Billerica, Mass.) for subsequent hybridization analysis. To examine gene expression in other human tissues, a commercially prepared blot was purchased containing 2 µg of polyadenylated heart, brain, placenta, lung, liver, kidney, skeletal muscle and pancreas RNA (Multiple Tissue Northern, Clontech, Palo Alto, Calif.).

Probes were prepared from cloned cDNA inserts using random hexamer primers and $^{32}$P-dCTP. The beta actin probe was generated using a previously described 1.4 kb cDNA (Alfieri, C., et al., *Virology* 181(2):595–608 (1991)). The glyceraldehyde phosphate dehydrogenase (GAPDH) probe was prepared from a commercially obtained DNA fragment (Clontech). Filters were hybridized for 18 to 24 h at 47° C. in a hybridization buffer consisting of 50% formamide, 6×SSPE (20×SSPE: 3.0M NaCl, 200 mM NaPO4, pH7.4, 20 mM EDTA), 1% SDS, 1×Denhardt's solution (100×Denhardt's: 2% BSA, 2% polyvinylpyrrolidone, 2% Ficoll), and 100 μ/ml sheared single-stranded herring testis DNA. Filters were washed according to the manufacturers' instructions, with high stringency washes performed at 67°–70° C. in 1 % SDS, 0.2×SSC, and exposed to preflashed film (X-OMAT AR, Kodak, Rochester, N.Y.) at −80° C. for 2 h to 10 days. Autoradiographic signal intensities were quantitated by densitometric scanning using a Beckman DU-8 spectrophotometer equipped with a slab gel Compuset Module. Induction factors were calculated for each probe as signal intensity ratios for EBV(+) versus EBV(−) cells, divided by the ratio of beta actin signal intensities.

cDNA library preparation. First strand cDNA was prepared from 5 μg polyadenylylated BL41/B95-8 RNA using Moloney murine leukemia virus reverse transcriptase (SuperScript, Bethesda Research Laboratories, Gaithersburg, Md.) and oligodeoxthymidylate primers in a 100 μL reaction. Second strand cDNA was synthesized using E. coli DNA polymerase I and RNAse H. The double stranded cDNA was blunt-ended with T4 DNA polymerase and EcoRI methylated. After ligation of EcoRI linkers, the cDNA was EcoRI restriction digested and size fractionated by gel filtration chromatography on Sepharose CL-4B. The purified cDNA was ligated to phosphorylated lambda gt10 arms (Promega, Madison, Wis.) and packaged (Gigapack Gold, Stratagene, La Jolla, Calif.).

Subtractive probe preparation. Radiolabelled cDNA was prepared from 6 μg of polyadenylylated BL41 or BL41/B95-8 RNA in a 200 μL reaction containing 50 μg/ml random DNA hexamers; 0.5 mM dATP, dGTP, dTTP; 25 μM unlabelled dCTP; 1.0 mCi $^{32}$P-dCTP (800 Ci/mMole, New England Nuclear); 2000 units recombinant Moloney murine leukemia virus reverse transcriptase. Reactions were 42° C. for 1 h. After precipitation, reaction products were resuspended in 0.1M NaOH and incubated 20 min. at 65° C. to hydrolyze RNA templates. Probes were neutralized with 0.1M acetic acid and size fractionated on G-50 Sephadex. Biotinylated RNA was prepared from polyadenylylated BL41 RNA using a photoactivatable azido-aryl biotin reagent (Photoprobe Biotin, Vector Laboratories, Burlingame, Calif.) following the manufacturer's protocol. Probe fractions were combined with 48 μg (for BL41/B95-8 probe) or 12 μg (for BL41 probe) biotinylated BL41 RNA and precipitated with ethanol. BL41/B95-8 probes were hybridized with an 8 fold excess (2 mg/ml) of biotinylated BL41 RNA; while BL41 control probes were hybridized with a 2 fold excess (0.5 μg/ml) of biotinylated BL41 RNA. Hybridizations and subtractions were performed using the "Subtractor" kit (Invitrogen, San Diego, Calif.) according to the manufacturer's instructions. The precipitated cDNA/RNA mixtures were resuspended in 10 to 20 μL H$_2$O and heated to 100° C. for 1 min. An equal volume of 2×hybridization buffer (Invitrogen) was added and the mixture was incubated at 65° C. for 20 to 24 h. Following addition of an equal volume of HEPES buffer (10 mM HEPES, pH 7.5, 1 mM EDTA), 20 μg streptavidin was added and the mixture was incubated on ice for 10 min. Biotinylated RNA and RNA:cDNA duplexes, complexed with avidin, were removed by repeated phenol/chloroform extractions. The single stranded, subtracted BL41 cDNA probe which remained in the aqueous phase was used directly for in situ filter hybridizations. Aqueous phase BL41/B95-8 cDNA probe was precipitated with ethanol and subjected to a second round of subtraction under identical conditions prior to use in filter hybridizations. Duplicate filters were made from 145 mm plates containing 6000 recombinant bacteriophage and were hybridized in parallel to equal amounts of BL41/B95-8 or BL41 subtracted probes. Filters were hybridized at 48° C. for 48 to 72 h in a buffer consisting of 50% formamide, 6×SSPE, 1% SDS, 10% dextran sulfate, 2×Denhardt's solution, 100 μg/ml sheared single-stranded herring testis DNA, and 10 μg/ml poly rA:rU (Sigma, St. Louis, Mo.). Filters were washed at 72° C. in 0.2×SSC and exposed 3 to 7 days to preflashed film (Kodak X-OMAT AR). Differentially expressed genes were identified by overlaying films from corresponding filters. Clones selected on primary screening were rescreened once at low density to verify differential expression and for plaque purification.

Analysis of clones. DNA was extracted from bulk liquid cultures of purified lambda gt10 clones and digested with EcoRI. cDNA inserts were purified by agarose gel electrophoresis and subcloned into pBluescript (+). Nucleotide sequences were determined and were compared by the BLAST algorithm (Altschul, S. F., et al., J. Mol. Biol. 215(3):403–10 (1990)) with known sequences resident in the National Center for Biotechnology Information databases using the Experimental GENINFO® BLAST Network Service, accessed through the Molecular Biology Computer Research Resource of the Dana-Farber Cancer Institute. Multiple sequence alignments were performed by the method of Higgins and Sharp (Higgins and Sharp, Gene 73(1):237–44 (1988)) using the CLUSTAL program (PCGene, IntelliGenetics, Mountain View, Calif.) with open gap and unit gap costs of 10.

Chromosome Mapping. Human metaphase cells were prepared from phytohemagglutinin-stimulated peripheral blood lymphocytes. The EBI-3 probe was prepared using a 1.09 kb truncated cDNA clone from which the AT-rich sequences of the Alu repeat were deleted. Fluorescence in situ hybridization was performed as described in Rowley et al., Proc. Natl. Acad. Sci. USA 87:9358–62 (1990). Biotin-labeled probes were prepared by nick-translation using Bio-11-dUTP (Enzo Diagnostics). Hybridization was detected with fluorescein-conjugated avidin (Vector Laboratories), and chromosomes were identified by staining with 4,6-diamino-2-phenylindole-dihydrochlohoride (DAPI).

Antibody Preparation. A DNA fragment encoding most of EBI-3 was synthesized by polymerase chain reaction amplification of EBI-3 recombinant bacteriophage template using oligonucleotide primers 10.7A (5' ACTGAATTCGAGCTC-CTGGCCTCAAG 3') (SEQ ID NO:7) and 10.7B (5' AAG-GATCCCCAGCAGCTCTGACACTG 3') (SEQ ID NO:8). EcoRI and BamHI restriction sites incorporated into the 10.7A and 10.7B primers, were used to clone digested amplification products in-frame into BamHI/EcoRI digested pGEX-2TK vector (Pharmacia). The resulting pGEX:EBI-3 construct directs synthesis of a fusion protein comprising glutathione-S-transferase (ST) linked to EBI-3 beginning with the proline residue at position 25, but lacking the signal peptide sequences. Following overnight culture, DH5alpha cells transformed with pGEX:EBI-3 plasmid were diluted 1 to 10 in fresh medium and induced 4 hours with 0.1 mM isopropyl-D-thiogalactopyranoside (IPTG). Fusion protein was purified from bacterial lysates by affinity chromatography on glutathione-sepharose, or by preparative electrophoresis from highly enriched bacterial "inclusion body" preparations, and was used to immunize rabbits (Pocono Rabbit Farms, Canadensis, Pa.). Immune rabbit serum was preabsorbed against purified GST coupled to agarose beads, and anti-EBI-3 antibodies were affinity purified by binding to a GST:EBI-3 fusion protein column. Immunoglobulin content was quantitated by polyacrylamide gel electrophoresis and Coomassie stain of serially-diluted affinity-purified serum and normal non-immune rabbit serum (NRS). Immunoglobulin concentration in affinity-purified preparations was typically 100- to 200- fold lower than in NRS.

Transfections. The protein coding region of the E-BI-3 cDNA was cloned into the EcoRI site of the eukaryotic expression vector, pSG5 (Stratagene). The resulting construct directs EBI-3 transcription under control of the SV40 late promoter. A EBI-3-Flag expression vector was constructed by PCR fusing a 6 amino acid kinase site (RRASVG) followed by an 8 amino acide FLAG sequence (DYKDDDDK) to the carboxy terminus of EBI-3 coding region. The resulting PCR product was cloned in the EcoRI site of pSG5. Approximately $1 \times 10^7$ target cells were transfected with 40 to 50 ug purified plasmid DNA by electroporation at 200 V, 960 uF in 0.4 cm cuvettes (BioRad, Hercules, Calif.). Plasmid DNA was purified by isopycnic banding on CsCl gradients.

Immunofluorescence. Tissue samples of placenta or excised tonsil were placed in dry ice/isopentane for frozen sections. Cultured IB4 or transfected BJAB cells were washed, placed on slides and air dried. Tissue section or cultured cell preparations were fixed 10 min. in a 50:50 mixture of acetone: methanol at −20° C. After rehydration, slides were incubated with affinity-purified anti-EBI-3 rabbit serum at 1:25 dilution in PBS/20% goat serum. Negative controls consisted of normal rabbit serum (Sigma) diluted 1:1250 in PBS/20% goat serum. After washing, antibody binding was detected with FITC-conjugated goat anti-rabbit antibody (1:500, Southern Biotechnology, Birmingham, Ala.) and was visualized using a Reichert Microstar IV fluorescence microscope. Frozen tonsil sections were double stained using anti-EBI-3 rabbit serum (1:25 diluted) and anti-CD22 mouse monoclonal antibody (1:50 diluted; Dako, Carpinteria, Calif.). Primary antibody binding was detected using FITC-conjugated goat anti-rabbit, and Texas Red-conjugated goat anti-mouse secondary antibodies. For live cell staining, incubated with rabbit anti-EBI-3 diluted 1:25, or NRS diluted 1:1250 in PBS/20% goat serum. Transfected COS7 cells were dissociated from culture flasks with 1 mM EDTA/PBS and stained in suspension under identical conditions.

Immunoblotting. Samples of cultured cells ($1 \times 10^7$ cells) in logarithmic growth, or fresh placenta samples (100 mg) were washed in PBS, solubilized in protein sample buffer (125 mM TRIS, pH 6.8, 4% SDS, 20% glycerol, 10% mercaptoethanol, 0.05% bromophenol blue), sonicated and boiled for 5 minutes. Extracts representing $5 \times 10^5$ cells were loaded into each lane. Proteins were electrophoretically separated on a 12% polyacrylamide-SDS gel and transferred to nitrocellulose. After blocking, blots were incubated in PBS containing 2% bovine serum albumin, 0.05% Tween 20 and polyclonal anti-EBI-3 at 1:80 dilution at room temperature. Specific immunoglobulin binding was detected using $^{125}$I-labeled protein A.

Immunoprecipitation. IB4 cells were metabolically labeled for 18 h with 50 µCi/ml $^{35}$S-methionine (Trans $^{35}$S-label, ICN) in methionine free RPMI medium supplemented with 10% dialyzed fetal bovine serum. Transfected BJAB or COS7 cells were similarly labeled 24 h after electroporation for 18 to 24 h in methionine free RPMI or DMEM supplemented with 10% dialyzed fetal bovine serum. Labeled cells were washed in ice cold PBS and lysed in 0.2 to 0.4 ml digitonin lysis buffer (1% digitonin, 10 mM triethanolamine, pH 7.5, 150 mM NaCl) or NP40 lysis buffer (1% NP40, 20 mM Tris, pH 7.4, 150 mM NaCl, 3% Glycerol, 1.5 mM EDTA) containing 1 mg/ml BSA and protease inhibitors (1 mM PMSF, 1 µg/ml leupeptin, 1 µg/ml pepstatin). Lysates were centrifuged for 30 min at 14,000×G and precleared with NRS and Protein A-Sepharose (Pharmacia). Cleared extracts were then incubated at 0° C. for 60 min with affinity-purified anti-EBI-3 serum or with NRS. Immune complexes were bound to protein A-Sepharose and washed in digitonin lysis buffer. When immunoprecipitation was performed using anti-Flag M2 monoclonal antibody (International Biotechnologies, Inc., New Haven, Conn.), cell lysates were precleared with NMS and protein G-Sepaharose, and immune complexes bound to protein G-Sepharose.

N-glycanase Treatment. Anti-EBI-3 and NRS control immunoprecipitates were prepared from IB4 cells, washed once in digitonin buffer containing 1 mg/ml BSA, four times in digitonin buffer, twice in 0. 5M LiCl, 0.1M Tris pH 7.4, and once in 10 mM Tris, pH 7.4. Immune complexes were eluted from protein A Sepharose by boiling for 5 minutes in 100 µL 50 mM Tris, pH 7.4, 0.5% SDS, 50 mM β-mercaptoethanol. Aliquots (20 µL) of IB4 extracts precipitated with anti-EBI-3 or NRS were adjusted to 1.25% NP40 and incubated with or without 0.3 units N-glycanase (Genzyme, Boston, Mass.) for 18 hr at 37° C. Samples were boiled in SDS protein sample buffer and analyzed on 10% polyacrylamide gels.

Example 1
Identification of cDNA Clones of EBV Induced RNAs by Subtracted Probe Hybridization cDNA clones of RNA from an in vitro EBV-infected BL cell line, BL41/B95-8 [EBV(+) BL41], were differentially screened with an EBV(+) BL41 cDNA probe from which sequences complementary to EBV(−) BL41 cell RNA had been specifically removed, and with an EBV(−) BL41 control cDNA probe. Sequences complimentary to EBV(−) BL41 RNA were removed from the EBV(+) Bl45 RNA cDNA probes by two subtractions with an 8 fold excess of biotinylated EBV(−) BL41 RNA. Overall, 85–95% of the labeled EBV(+) BL41 probe was removed by the two subtractions. EBV(−) BL41 cDNA control probe was subtracted only once, removing 60–85% of the probe; thereby reducing hybridization to plaques containing cDNAs from abundant RNAs so that hybridization to cDNAs from less abundant BL41 RNAs was evident.

Seventy-five phage cDNA clones differentially hybridized to the EBV(+) BL41 probe on the first screen of 75,000 recombinant phage. Twenty-five clones were consistently positive on rescreening. The eighteen clones which demonstrated the greatest reactivity with the EBV(+) versus the EBV(−) BL41 cDNA probes were selected for nucleotide sequencing and RNA blot hybridization.

Example 2
Nucleotide Sequences of EBV Induced cDNAs

The first 12 clones are described in Table 1. Ten clones matched 7 previously characterized genes: two independent clones each of the complement receptor type 2 (CD21), the serglycin proteoglycan core protein and vimentin; and one clone each of cathepsin H, annexin VI (p68), the myristylated alanine-rich protein kinase C substrate (MARCKS) and the lymphocyte hyaluronic acid receptor (CD44). The 2.6 kb MARCKS cDNA precisely matched the previous 1.58 kb human MARCKS cDNA clone (Harlan, D. M., et al., J. Biol. Chem. 266(22):14399–405 (1991)) at its 5 prime end. The 3 prime untranslated region of the new clone is highly homologous to bovine MARCKS cDNA (Stumpo, D. J., et al., Proc. Natl. Acad. Sci. USA 86(11):4012–6 (1989)).

The two remaining clones are from novel RNAs, EBV induced genes 1 (EBI 1) and 2 (EBI 2), whose nucleotide sequences can be predicted to encode G-protein coupled peptide receptors. The complete nucleotide and deduced amino acid sequences of the EBI 1 and EBI 2 cDNAs are shown in FIGS. 1A and 1B, respectively. Because the first EBI 1 cDNA was 1.2 kb, significantly shorter than the 2.4 kb RNA, 20 other cDNA clones were obtained using the initial cDNA as a probe. The largest clone is 2153 nucleotides (nt) and has a 1134 nt open-reading frame (FIG. 1A). This clone is probably nearly full length, since it is close to the expected size, considering it has only a short poly A tail. Translation is likely to initiate from either of two AUGs, at nt 64–66 or 82–84, the first of which conforms to a consensus translational initiation sequence (Kozak, M., *J. Biol. Chem.* 266 (30):19867–70 (1991)). An in-frame stop codon at nt 10–12 is consistent with downstream initiation at nt 64–66. The polypeptide encoded by the sequence beginning at nt 64 has a predicted molecular weight of 42.7 kD and includes eight hydrophobic domains likely to mediate membrane insertion. The first hydrophobic domain begins at the amino terminus and ends at a predicted signal peptidase cleavage site. The 7 remaining hydrophobic domains are characteristic of the G-protein coupled receptor family. Potential asparagine linked glycosylation sites are present in the extracellular amino terminal segment and in the third extracellular loop.

Since the initial EBI 2 cDNA was 1643 nt and approximated the size expected from a 1.9 kb polyadenylated RNA, further cDNA clones were not obtained. The EBI 2 cDNA contains a 1083 nt open reading frame with two methionine codons are at nt 34–36 and 46–48 (FIG. 1B). Although neither methionine codon is in a favored initiation context (Kozak, M., *J. Biol. Chem.* 266(30):19867–70 (1991)), an upstream, in-frame termination codon and the absence of other potential open reading frames is consistent with translation initiating at the first or second methionine codon. Initiation at the first would result in a 41.2 kD protein. The deduced amino acid sequence predicts 7 hydrophobic transmembrane segments in the characteristic configuration of G-protein coupled receptors. In contrast to the EBI 1 protein, EBI 2 lacks a signal peptide. A possible N-linked glycosylation site is found in the amino terminal extracellular domain. Though the EBI 2 cDNA lacks a polyadenylate tail, a canonical polyadenylation signal (AATAAA) near the 3 prime end is consistent with the cDNA being essentially complete.

TABLE 1

Summary of EBV Induced RNA:cDNA Clones

| Clone | Gene | cDNA Size (kb) | RNA Size (kb) | Induction[1] |
|---|---|---|---|---|
| 1.1 | CD44 | 1.3 | 1.6, 2.2, 5.0 | >100X |
| 3.3; 7.3 | CD21 | 2.1; 1.8 | 4.8 | |
| 6.5 | MARCKS | 2.6 | 2.9 | 30X |
| 8.2 | Cathepsin H | 1.5 | 1.7 | 6X |
| 10.4; 11.4 | Serglycin | 1.1; 1.1 | 1.4 | 3.5X |
| 12.3 | Annexin VI | 2.3 | 3.0 | 5X |
| 12.5; 13.0 | Vimentin | 1.0; 1.8 | 2.0 | |
| 6.4 | EBI 1 | 1.2 (2.14)[2] | 2.4 | 21X |
| 3.2 | EBI 2 | 1.64 | 1.9 | >200X |
| | Beta actin | | 2.2 | 3X[3] |

[1]Induction levels were calculated as ratio of signal intensities (BL41/B95-8 to BL41) for individual probes, divided by ratio of signal intensities for Actin probe.
[2]The 1.2 kb EBI 1 clone identified on initial screen was incomplete. Rescreening of the cDNA library resulted in isolation of several additional full-length clones, the largest of which was 2.14 kb.
[3]Induction of beta actin RNA was calculated as ratio of actin signal intensities, to ratio of signal intensities for glyceraldehyde phosphate dehydrogenase probe.

Example 3
Comparison of EBI 1 and 2 with other G protein coupled receptors

The EBI 1 and EBI 2 nucleotide and predicted amino acid sequences were compared with the Genbank (release 72 and updates), EMBL (release 31), Genbank translation, Swiss protein (release 22) and Protein Identification Resource (PIR, release 33) databases, using the BLAST algorithm (Altschul, S. F., et al., *J. Mol. Biol.* 215(3):403–10 (1990)). EBI 1 and EBI 2 are homologous to G protein associated receptors. EBI 1 is highly homologous to the human high or low affinity interleukin 8 (IL-8) receptors at both the nucleotide (data not shown) and amino acid sequence levels. IL8 receptor itself is not expressed on lymphocytes (Holmes, W. E., et al., *Science* 253(5025):1278–80 (1991); Murphy and Tiffany, et al., *Science* 253:1280–1283 (1991)). Excluding the putative EBI 1 signal peptide, the overall amino acid identity among the 3 proteins exceeds 30%, with conservative changes observed at many of the non-identical residues. The identity increases to 40% when EBI 1 is compared with either IL-8 receptor individually. Additional similarities with the IL-8 receptors include a high proportion of serine and threonine near the carboxy terminus, and a highly acidic amino terminal extracellular domain. The IL-8 receptor acidic residues are implicated in binding IL-8 basic amino acids (Holmes, W. E., et al., *Science* 253(5025):1278–80 (1991); Murphy and Tiffany, et al., *Science* 253:1280–1283 (1991).

The EBI 2 gene does not have such a close homologue. EBI 2 has 24% amino acid identity to the thrombin receptor (Vu, T. K., et al., *Cell* 64(6):1057–68 (1991)). Less extensive homologies are observed with a number of other G-protein coupled receptors, including the receptors for vasoactive intestinal polypeptide, somatostatin (type 1) and angiotensin II, as well as the low affinity IL-8 receptor. EBI 2 also exhibits more distant homologies with EBI 1 and the high affinity IL-8 receptor. Significantly, these are the same proteins which, in different order, exhibit the closest homologies with the EBI 1 protein. Together they constitute a subfamily of G-protein coupled peptide receptors. The greatest conservation of residues among these proteins extends from the first transmembrane domain to the second intracellular loop. Because of the particular conservation of an amino acid sequence among these G protein coupled receptors, we are able to identify a new highly conserved sequence motif at the carboxy end of TM III and the adjacent second intracellular loop. This motif, S-(I/L)-D-R-(Y/F)-X-X-X-X, with x being a hydrophobic amino acid, is in a wide variety of G-protein coupled receptors; and is not in other proteins in the data bases surveyed. Other highly conserved features of G protein coupled receptors in EBI 1 and 2 include the asparagine in TM I, the proline in TM II, the aspartate in the first intracellular loop, and the tryptophane and cysteine in the first extracellular loop. This cysteine has been postulated to be involved in disulfide linkage to a conserved cysteine present in the second extracellular loop in several other receptors, including the beta adrenergic and thrombin receptors.

Example 4
Analysis of induced gene expression by RNA blot hybridization

Probes from seven of the nine EBV induced cDNAs were hybridized to identical blots of polyadenylated RNA from the EBV(+) or EBV(−) BL41 cell lines or from the EBV transformed lymphoblastoid cell line, IB4 (FIG. 2). Vimentin and CD21 were previously shown to be EBV induced and were not further evaluated. The RNAs loaded in the EBV(+), BL41, and EBV(−) BL41 lanes were standardized with respect to beta actin reactivity. Significantly less IB4 cell RNA was used due to the high abundance of the putative induced gene RNAs in these cells (FIG. 2, Actin probe). Probes from each of the cDNA clones detected RNAs which are significantly more abundant in both IB4 and EBV(+) BL41 cells than in EBV(−) BL41 cells. Induction factors indicated in Table 1 were determined by quantitative densitometric scanning of autoradiographs and reflect the fold enhancement of signal intensities in EBV(+) BL41 cells compared with EBV(−) BL41 cells, corrected for the ratio of actin reactivities. Standardization by actin reactivity, however, significantly underestimates the absolute induction levels since actin is induced 3-fold by EBV infection of BL41 cells relative to glyceraldehyde phosphate dehydrogenase, (GAPDH), or to total RNA amounts quantitated spectrophotometrically. To achieve equal actin signal intensities, 3-fold more EBV(−) BL41 than EBV(+) BL41 RNA was loaded per lane. Importantly, each of the RNAs was at least as abundant in IB4 cells relative to GADPH as in EBV(+) BL41 (FIG. 2).

EBI 1, EBI 2, CD44 and MARCKS are the most induced of the seven genes. The CD44 gene encodes three distinct RNAs of 1.6, 2.2 and 4.8 kb respectively in both IB4 and EBV(+) BL41 cells. No CD44 RNA was detected EBV(−) BL41 cells even after prolonged autoradiographic exposures. EBI 2 RNA was also undetectable in EBV(-) BL41 cells.

Example 5

Expression of EBI 1 and 2 in human cell lines and tissues

The expression of EBI 1 and 2 in human cell lines and tissues was evaluated by hybridizing actin, EBI 1 or EBI 2 probes to blots of cell line or tissue RNAs. While EBI 1 is weakly expressed in BL41, EBI 2 is not; and, neither EBI 1 nor EBI 2 are expressed in another EBV(−) BL cell line, BL30 (FIG. 3). EBI 1 and EBI 2 RNAs are abundant in primary human lymphocytes transformed by EBV in vitro and propagated as continuous lymphoblastoid cell lines for several years (IB4) or for less than 1 year (W91-LCL) (FIG. 3). EBI 1 RNA is faintly detectable in the human T cell line Jurkat, and is abundantly expressed in a second T cell line, HSB-2 (FIG. 3). EBI 2 RNA is not detected in either T cell line (FIG. 3), nor in a third T cell line, MOLT-4. EBI 1 is not expressed in the human promyelocytic line, HL60, the chronic myelogeneous leukemia cell line K562, the epithelial cell line, RHEK-1, the fibroblast-like osteosarcoma cell line, TK143, or the monocytic cell line, U937 (FIG. 3). EBI 2, however, is expressed weakly, relative to actin, in HL60, U937 (U937 RNA is partially degraded) or HeLa cells (FIG. 3).

EBI 1 and 2 RNAs are abundant in human spleen, somewhat less abundant relative to actin in tonsil and are not detectable in bone marrow (FIG. 3). Both genes were expressed in resting PBMCs at levels comparable to IB4 or LCL-W91 B lymphoblastoid cells (FIG. 3). Expression increased in parallel cultures stimulated for 72 h with pokeweed mitogen (PWM), although actin expression also increased with PWM (FIG. 3). The EBI 1 and 2 RNA in stimulated and non stimulated PBMC cultures is likely to be mostly in B lymphocytes since EBI 1 RNA is at low levels and EBI 2 RNA is absent from phytohemagglutinin stimulated, PBMC derived, T lymphocytes (FIG. 3). These findings are consistent with expression patterns observed in T cell lines.

EBI 1 and 2 RNA levels were also evaluated in a variety of non-hematopoietic human tissues. The EBI 1 probe detects small amounts of RNA in both lung and pancreas (FIG. 4). Rehybridization of this blot with an immunoglobulin mu chain probe (FIG. 4, Igu probe) indicated that these tissue preparations contained significant amounts of immunoglobulin RNA, probably due to B lymphocytes in the tissues. Since EBI 1 RNA is abundant in peripheral blood lymphocytes, the EBI 1 RNA in the lung and pancreas is likely to be due to B lymphocytes. Similarly, the low level of EBI 2 RNA detected in pancreatic tissue is probably due to infiltrating B lymphocytes (FIG. 4). However, the abundance of EBI 2 RNA in the lung is too great to attribute to lymphocyte contamination and is more likely due to specific expression in pulmonary epithelial cells or macrophages (FIG. 4).

Example 6

Cloning and Characterization of EBI 3

Subtractive hybridization screening of a BM41/B95-8 cDNA library has permitted the identification of a number of genes expressed at higher levels in EVB-infected BL cells compared with matched EBV(−) cells. Twenty-five putative EBV-induced gene clones were initially isolated. Of these, 13 clones matched 8 previously known genes. The remaining 12 clones represented 10 novel genes. Two of these clones were derived from transcripts of a previously uncharacterized gene designated EBV-induced gene 3 (EBI 3).

The complete nucleotide and amino acid sequence of the larger EBI 3 clone are shown in FIG. 5 (SEQ ID NO:5 and SEQ ID NO:6, respectively). The 1161 nucleotide cDNA contains a 687 nucleotide open reading frame. A unique AUG codon preceding this reading frame at nucleotides 14–16 conforms to the Kozak consensus translational initiation sequence. Initiation from this site results in the synthesis of a polypeptide with a predicted molecular mass of 25,380 Daltons. The first 20 amino acids are highly hydrophobic and likely form a signal peptide for membrane translocation with a predicted signal peptidase cleavage site following a glycine residue at position 20. Two potential asparagine-linked glycosylation sites are also identified. However, no other hydrophobic segments capable of forming the transmembrane domain of an integral membrane protein are evident. To verify the structure of this cDNA, five additional clones were retrieved from the library. All of these exhibited identical sequences throughout the putative carboxy-terminal portion of the predicted protein. The 3' end of the EBI 3 nucleotide sequence is notable for its homology to the left monomer of the human Alu repeat element. This homology extends to and includes the A-rich sequences which immediately precede the polyadenylate tail of the mRNA.

The EBI 3 nucleotide and amino acid sequences were compared with all known sequences of Genbank nucleic acid, and Genbank translation, Protein Identification Resource (PIR) and Swiss Protein databases, respectively, using the Experimental GENINFO(R) BLAST-server network of the National Center for Biotechnology Information. No significant nucleotide homologies were observed, excluding matches with the 3' untranslated Alu repeat. However, the predicted EBI 3 protein is approximately 30% identical to the receptor for ciliary neurotrophic factor (CNTF), with conservative amino acid changes at many of the non-identical residues. Of particular significance is the pattern of conserved residues which include 4 cysteines at positions 35, 46, 80 and 90 respectively of the complete EBI 3 protein sequence; tryptophanes at positions 48 and 150; proline at position 125; and aliphatic hydrophobic residues at positions 128, 136, 148 and 204. In addition, the EBI 3 sequence LSDWS at residues 215 to 219 closely matches the WSDWS sequence of the CNTF receptor. These conserved structural features are characteristic of and unique to members of the cytokine receptor family. The predicted EBI 3 protein exhibits less extensive homologies with the p40 subunit of interleukin 12 (IL-12), also known as natural killer cell stimulatory factor. Though a secreted protein, IL-12 p40 possesses the same conserved residues and is also a member of the cytokine receptor family. In addition, the carboxy terminal 100 amino acids of the EBI 3 protein exhibit structural homologies with type III fibronectin domains of a variety of adhesion related molecules, including tenascin, cytotactin and the neural cell adhesion molecule, NCAM. This feature has also been described among other cytokine receptor family members.

Example 7
The EBI-3 Gene Localizes to Chromosomes 19, Band p13.3

To localize the EBI-3 gene, biotin-labeled EBI-3 cDNA was hybridized to normal human metaphase chromosomes. The EBI-3 probe resulted in specific labeling only of chromosome 19. Specific labeling of 19p13 was observed on one (1 cell), two (8 cells), three (3 cells) or all four (6 cells) chromatids of the chromosome 19 homologues in 18 cells examined. Of 53 signals observed, 29 or (55%) were at 19p13.3, 17 or (32%) were at the junction of 19p13.2 and p13.3, and 4 (8%) were at 19p13.2. One signal was at 4p16, 3cen, or 3q26.2 (2% each). Similar results were obtained in another hybridization experiment using this probe. These results indicate that the EBI-3 gene is at chromosome 19, band p13.3.

Example 8
EBI-3 RNA Is Expressed in EBV-infected Lymphocytes and Placenta

Hybridization of a $^{32}$P-labeled EBI 3 probe to RNA blots detects a 1.5 kb RNA in the EBV-infected cell lines IB4 and BL41/B95-8 (FIG. 6). EBI 3 RNA is undetectable, however, in the EBV(−) control cell line BL41. To provide standards for the amounts of RNA loaded in each line, parallel blots were hybridized with probes for glyceraldehyde phosphate dehydrogenase (GAPDH) and actin. These probes indicate that the BL41 lane contains as much or more RNA than the EBV-infected cell lanes.

Figure 7A:
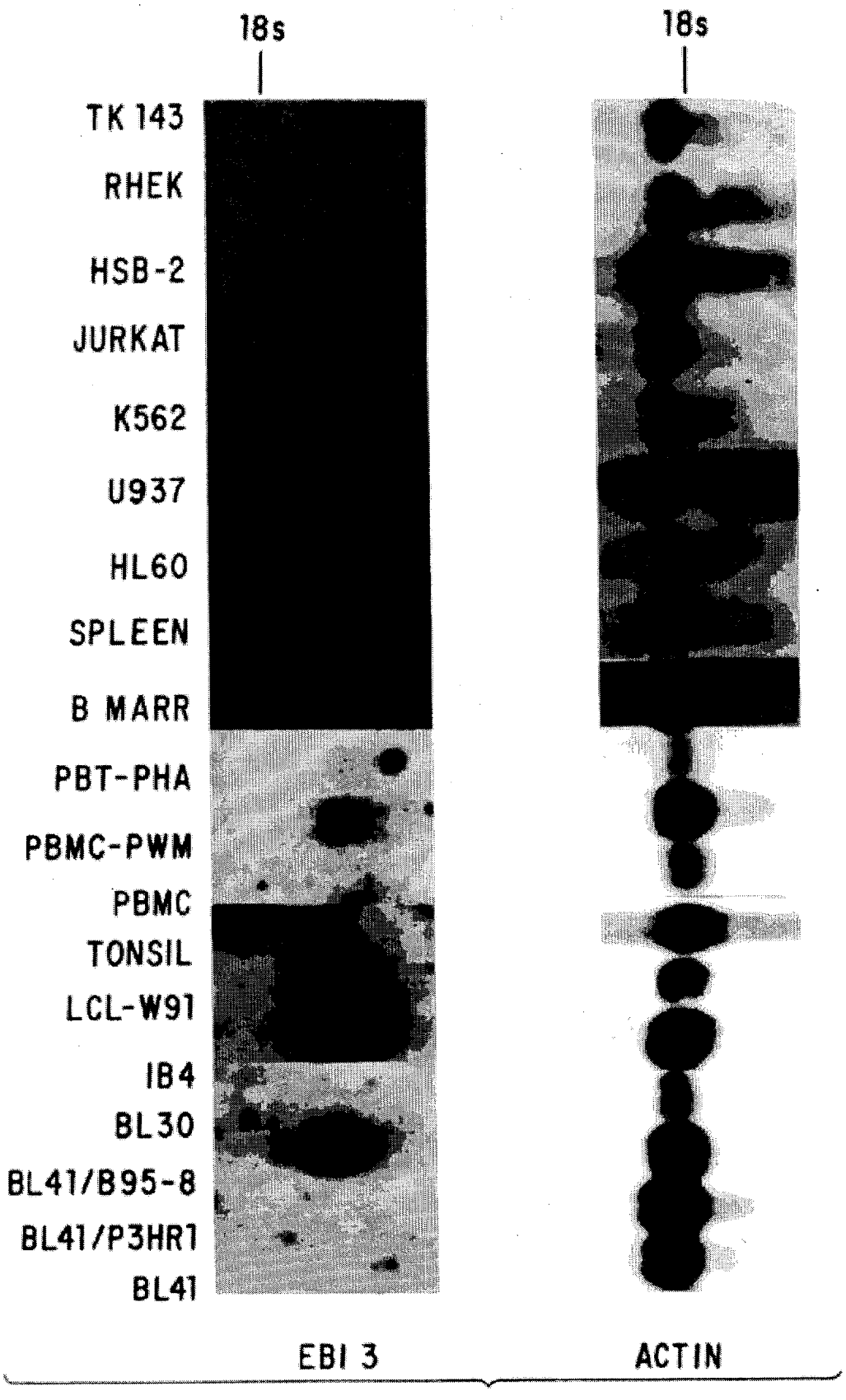

Densitometric analysis of autoradiographs of EBI-3 and β actin hybridized blots indicate that BL41/B95-8 and IB4 cells contain at least 200-fold more EBI-3 RNA, relative to actin RNA levels, than do BL41 cells. Examination of a series of human cell lines demonstrated that EBI-3 is expressed at high levels in two other EBV-transformed LCLs, W91 and SLA, but is undetectable in T-cell lines MOLT-4 and Jurkat, and in the EBV-negative BL cell lines, Louckes and BJAB (FIG. 7A). EBI-3 RNA was also detected at low levels in several non-lymphoid cell lines, including K562, TK143, RHEK-1 and HeLa, but was not detectable in U937 or HL60 myelocytic cell lines. Analysis of human lymphoid tissues indicated that EBI-3 RNA is present at low levels in normal unfractionated cells of tonsil and at significantly higher levels in spleen, but is undetectable in resting peripheral blood mononuclear cells (PBMC) and in bone marrow. However, EBI-3 mRNA is induced in PBMC by stimulation with the B and T lymphocyte activating agent, pokeweed mitogen (PWM).

Figure 7B:
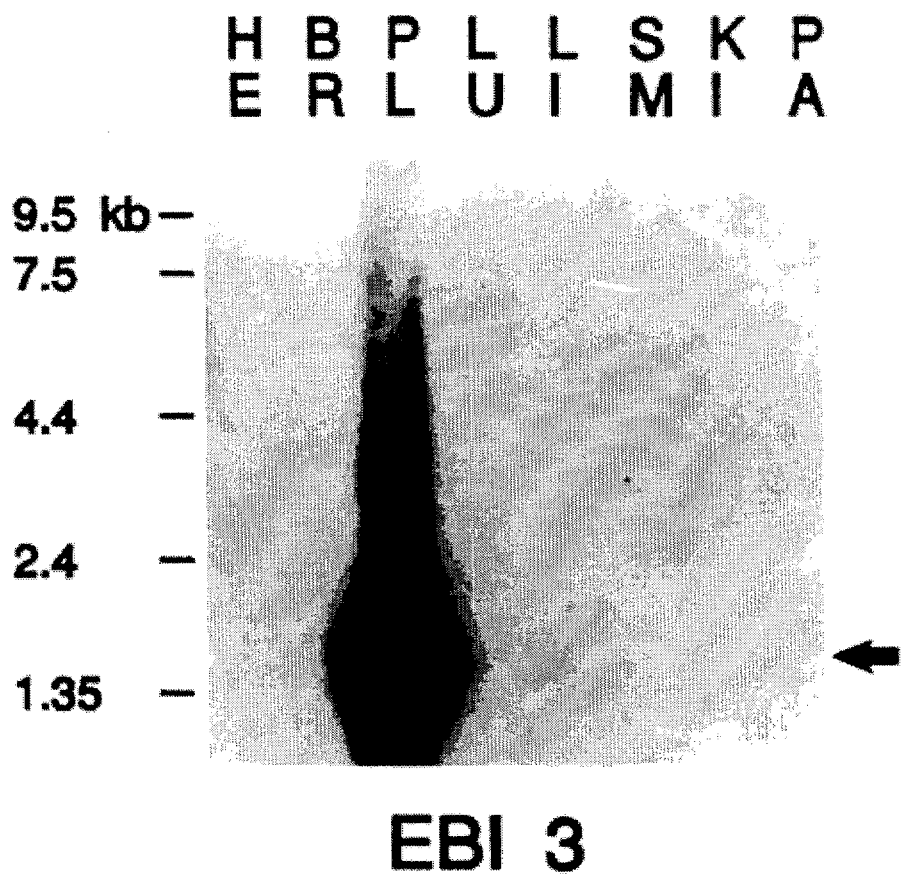

Expression of EBI 3 RNA was also analyzed in a variety of non-lymphoid human tissues (FIG. 7B). Abundant expression was observed in placenta, significantly exceeding expression levels observed in any lymphoid cell type. Shorter exposures of this blot indicated that EBI-3 is expressed in placenta as a single 1.4 kb RNA species. EBI 3 RNA was also faintly detectable in liver RNA. However, rehybridization of this blot with an immunoglobulin μ heavy chain probe indicated detectable Ig gene expression, probably due to infiltration of liver tissue with lymphocytes in vivo. The apparent expression of EBI 3 in liver could therefore be due to expression in resident lymphocytes.

Example 9
EBI-3 Encodes A Secreted Glycoprotein

Polyclonal EBI-3-specific antiserum was raised in rabbits immunized with GST:EBI-3 fusion protein. The affinity purified antibody recognized a 33 kD protein in extracts from fresh post-partum placenta and from EBV-positive BL41/B95-8 or IB4 cells. This protein was not detected in extracts from EBV-negative BL41 cells. A protein of identical size was also detected in lysates of BJAB or COS7 cells transfected with EBI-3 cDNA cloned into the expression vector, pSG5, but was not present in control COS7 cells transfected with the pSG5 expression vector alone, and was barely detectable in control BJAB cells. The small amount of EBI-3 protein present in pSG5 transfected BJAB control cells is consistent with the low EBI-3 RNA levels detected in RNA blot hybridizations. These results confirm that the EBI-3 cDNA is the complete reading frame of genomic EBI-3 gene transcripts. The absence of larger EBI-3 proteins is also consistent with the RNA blot and cDNA cloning experiments which identify a single EBI-3 transcript. In addition to the predominant 33 kD protein, immunoblots of EBI-3-transfected BJAB and COS7 cells also detected proteins of 30 kD and a 24–25 kD doublet. The 30 kD species was also detectable in placental lysates. These likely represent incompletely processed forms of the protein or stable degradation products.

Since the EBI-3 protein is not predicted to include a transmembrane domain, experiments were done to determine whether EBI-3 is expressed as a soluble molecule. Filtered supernatants from transfected COS7 or BJAB cell cultures were analyzed by immunoblotting. A 34 kD protein was present in supernatants from COS7 cells transfected with EBI-3 cDNA, but was undetectable in supernatants of pSG5 vector transfected control cells. With long autoradiographic exposures, the 34 kD EBI-3 was also detectable in EBI-3-transfected BJAB supernatants, but at much lower abundance than in COS7 supernatants. The soluble protein from both COS7 and BJAB supernatants is distinctly larger than the protein detected in cell lysates. To confirm these findings, supernatants from $^{35}$S-methionine-labeled, EBI-3-transfected BJAB B lymphocytes or COS7 cells were immunoprecipitated using polyclonal anti-EBI-3 serum. This antibody specifically precipitated a 34 kD protein which was not detected in immunoprecipitates of pSG5 vector transfected control BJAB or COS7 cell supernatants, or in supernatants precipitated with serum from normal, non-immunized rabbits. The secreted protein is slightly larger than the protein from cell lysates. Although EBI-3 was detectable in lysates of IB4 cells, EBI-3 was not detectable in IB4 cells supernatants, by either immunoblot or immunoprecipitation.

Example 10
EBI-3 is N-glycosylated

The 33/34 kD EBI-3 proteins are significantly larger than the 23 kD signal peptidase cleavage product predicted from the primary sequence. To test the possibility that the potential N-linked glycosylation sites are utilized, $^{35}$S-labeled EBI-3 was immunoprecipitated from IB4 cell lysates and incubated in vitro with N-glycanase to remove asparagine-linked carbohydrate. The expected 33 kD EBI-3 protein was observed in untreated IB4 immunoprecipitates. N-glycanase treatment resulted in a reduction of EBI-3 molecular mass from 33 kD to 28 kD. It is unlikely that this shift resulted from protease degradation of EBI-3 since other proteins non-specifically coprecipitated with EBI-3 failed to show changes in relative molecular mass or band intensities.

Example 11
EBI-3 is in the Cytoplasm and on the Plasma Membranes of cells

Immunostaining of fixed, EBV-transformed IB4 cells demonstrated pan cytoplasmic fluorescence with a reticular pattern. BJAB B lymphocytes or COS7 cells transfected with EBI-3 cDNA exhibit qualitatively similar patterns, but significantly greater staining intensity. Scattered transfected cells also showed weak plasma membrane staining. A similar pattern of staining was observed in EBI-3-Flag transfected BJAB or COS7 cells stained with the anti-Flag M2 monoclonal antibody. IB4, COS7 or BJAB cells expressing EBI-3 and stained with NRS were uniformly negative in all experiments, as were BJAB and COS7 control cells transfected with pSG5 vector and stained with anti-EBI-3 serum. The cytoplasmic staining pattern probably reflects accumulation or retention of EBI-3 in the endoplasmic reticulum.

To determine whether EBI-3 is also on the cell plasma membrane, live IB4, and transfected BJAB or transfected COS7 cells were stained in suspension and the polyclonal anti-EBI-3 rabbit serum. In IB4 lymphocytes, faint membrane fluorescence was observed on the majority of cells. This staining was substantially weaker than the cytoplasmic staining exhibited by fixed cells. More intense live cell plasma membrane staining was observed in both BJAB B lymphocytes and COS7 cells transiently or stably transfected with EBI-3 cDNA. Fluorescence staining of live pSG5 vector transfected control cells was not detected with anti-EBI-3 serum, and staining of EBI-3 transfected or IB4 cells was not observed using NRS.

Example 12
EBI-3 Staining of Human Tissues

Samples of placental tissues were obtained immediately post-partum and analyzed by immunofluorescence using rabbit polyclonal anti-EBI-3 serum. EBI-3 protein was detected in trophoblast cells lining placental villi with a diffuse cytoplasmic staining pattern and perinuclear accentuation. Expression of EBI-3 by trophoblastic cells was confirmed by in situ hybridization with a EBI-3 anti-sense RNA probe. Analysis of frozen sections of human tonsil by immunofluorescence demonstrated EBI-3 protein in scattered mononuclear cells of interfollicular zones. These cells exhibited strong cytoplasmic staining in a reticular pattern, similar to that observed in cultured cell lines. The EBI-3-positive cells have abundant cytoplasm and indented nuclei which were often larger than nuclei of neighboring lymphocytes. Tissue sections stained simultaneously with rabbit anti-EBI-3 and the mouse monoclonal antibody, anti-CD22 by two color immunofluorescence indicated that EBI-3-positive cells fail to express the B cell marker, CD22. The morphology and location of EBI-3-producing cells suggest these may be macrophages or T cells. Normal, non-immune rabbit serum controls were negative, indicating that the fluorescence did not result from rabbit Ig binding to Fc receptors. Frozen sections of human spleen stained with anti-EBI-3 serum revealed a highly restricted distribution of EBI-3-positive cells in marginal zones of periartiolar sheaths and lymphoid follicles. EBI-3-positive cells were significantly more abundant in spleen than in tonsil, consistent with the RNA hybridization results which detect more EBI-3 RNA in splenic tissues.

Example 13

Normal PBMC were cultured 4 days $1 \times 10^6$ cells/mL in RPMI 1640 supplemented with 10% FBS and with 10 µg/ml PHA. Cells were washed, recultured ($1 \times 10^6$/well in 0.2 ml RPMI 1640/10% FBS) with or without IL-12 (4 ng/ml) or IL-2 (100 ng/ml). Also added alone or with IL-12 or IL-2 were Genetics Institute purified p40, MB-pSG5 SN, or MB-EBI3 SN (both concentrated 7× and buffer exchanged to PBS). The cultures were incubated for additional 3 days, pulsed with $^3$H-thymidine, and incorporated radioactivity was measured.

Purified p40 dose-dependently inhibited IL-12 bioactivity. EBI-3 but not the pSG SN control also dose-dependently inhibited IL-12 bioactivity. Neither p40 nor EBI-3 inhibited IL-2 induced T cell proliferation.

|  | added | Conc. | CPM |
|---|---|---|---|
| PHA-activated MNC | none |  | 364 |
| $1 \times 10^5$/well | IL-2 | 100 ng/ml | 104,823 |
|  | IL-12 | 4 ng/ml | 7,526 |
|  | p40 | 1 µg/ml | 805 |
|  | p40 | 500 ng/ml | 507 |
|  | p40 | 250 ng/ml | 249 |
|  | MB pSG SN | neat | 502 |
|  | " | 1:2 | 391 |
|  | " | 1:4 | nd |
|  | MB EBI-3 SN | neat (~2µg/ml) | 324 |
|  | " | 1:2 | 332 |
|  | " | 1:4 | 267 |
| PHA + IL-12 4 ng/mL | p40 | 1 µg/ml | 1,003 |
|  | p40 | 500 ng/ml | 4,847 |
|  | p40 | 250 ng/ml | 5,731 |
|  | MB pSG SN | neat | 8,351 |
|  | " | 1:2 | 7,418 |
|  | " | 1:4 | 6,083 |
|  | MB EBI3 SN | neat | 544 |
|  | " | 1:2 | 3,117 |
|  | " | 1:4 | 6,375 |
| PHA + IL-2 100 ng/mL | p40 | 1 µg/ml | 102,681 |
|  | " | 500 ng/ml | 117,249 |
|  | " | 250 ng/ml | 112,842 |
|  | MB pSG SN | neat | 161,047 |
|  | " | 1:2 | — |
|  | " | 1:4 | — |
|  | MB EFI 3 SN | neat | 156,737 |

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A method of assessing or monitoring fetal or placental development comprising:

a) taking a maternal serum sample from a patient;

b) detecting the level or size of EBI-3 nucleic acid or EBI-3 protein in said sample to obtain a first result wherein said fetal or placental development is assessed or monitored by comparing said first result with a control result.

2. The method of claim 1, wherein the level or size of EBI-3 protein in said sample is detected.

3. The method of claim 1, wherein the level or size of a nucleic acid which encodes EBI-3 protein in said sample is detected.

* * * * *